US006322771B1

(12) United States Patent
Linden et al.

(10) Patent No.: US 6,322,771 B1
(45) Date of Patent: Nov. 27, 2001

(54) INDUCTION OF PHARMACOLOGICAL STRESS WITH ADENOSINE RECEPTOR AGONISTS

(75) Inventors: Joel M. Linden; David K. Glover; George A. Beller; Timothy MacDonald, all of Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/336,198

(22) Filed: Jun. 18, 1999

(51) Int. Cl.[7] .................................................. A61B 5/055
(52) U.S. Cl. ........................ 424/9.3; 424/1.11; 424/9.1; 424/9.4; 424/9.5; 536/27.6
(58) Field of Search .................. 424/1.11, 1.65, 424/9.1, 9.3, 9.4, 9.5, 9.6, 9.7, 9.8, 1.81, 1.85; 544/224, 225, 228, 230, 231, 233, 235, 271, 277; 536/27.6, 26.7, 26.26

(56) References Cited

U.S. PATENT DOCUMENTS

| | | |
|---|---|---|
| Re. 36,494 | 1/2000 | Olsson et al. ............. 514/46 |
| 3,892,777 | 7/1975 | Gruenman et al. ............. 260/340.5 |
| 4,193,926 | 3/1980 | Schmiechen et al. ............. 260/326 |
| 4,242,345 | 12/1980 | Brenner et al. ............. 424/253 |
| 4,665,074 | 5/1987 | Amschler ............. 514/247 |
| 4,824,660 | 4/1989 | Angello et al. ............. 424/1.1 |
| 4,879,296 | 11/1989 | Daluge et al. ............. 514/263 |
| 4,938,949 | 7/1990 | Borch et al. ............. 424/10 |
| 4,956,345 | 9/1990 | Miyasaka et al. ............. 514/46 |
| 4,965,271 | 10/1990 | Mandell et al. ............. 514/263 |
| 5,070,877 | 12/1991 | Mohiuddin et al. ............. 128/653.4 |
| 5,096,906 | 3/1992 | Mandell et al. ............. 514/263 |
| 5,124,455 | 6/1992 | Lombardo et al. ............. 546/181 |
| 5,140,015 | 8/1992 | Olsson et al. ............. 514/46 |
| 5,189,027 | 2/1993 | Miyashita et al. ............. 514/46 |
| 5,272,153 | 12/1993 | Mandell et al. ............. 514/263 |
| 5,278,150 | 1/1994 | Olsson et al. ............. 514/46 |
| 5,298,508 | 3/1994 | Jacobson et al. ............. 514/263 |
| 5,565,462 | 10/1996 | Eitan et al. ............. 514/262 |
| 5,593,975 | 1/1997 | Cristalli ............. 514/46 |
| 5,665,754 | 9/1997 | Feldman et al. ............. 514/397 |
| 5,668,139 | 9/1997 | Belardinelli et al. ............. 514/263 |
| 5,696,254 | 12/1997 | Mansour et al. ............. 536/27.11 |
| 5,731,296 | 3/1998 | Sollevi ............. 536/46 |
| 5,756,706 | 5/1998 | Mansour et al. ............. 536/27.11 |
| 5,854,081 | 12/1998 | Linden et al. ............. 436/501 |
| 5,877,180 | 3/1999 | Linden et al. ............. 514/266 |
| 5,932,558 | 8/1999 | Cronstein et al. ............. 514/46 |
| 5,998,386 | 12/1999 | Feldman ............. 514/46 |
| 6,004,945 | 12/1999 | Fukunaga ............. 514/46 |
| 6,020,321 | 2/2000 | Cornstein et al. ............. 514/46 |
| 6,020,339 | 2/2000 | Perrier et al. ............. 514/269 |
| 6,034,089 | 3/2000 | Han et al. ............. 514/269 |

FOREIGN PATENT DOCUMENTS

| | | | |
|---|---|---|---|
| 0700908 | 3/1996 | (EP) | ............. C07D/239/54 |
| 99/63938 | 12/1999 | (WO) | . |
| 9847509 | 10/1998 | (WO) | ............. A61K/31/415 |
| 9511681 | 5/1995 | (WO) | ............. A61K/31/52 |
| 9604280 | 2/1996 | (WO) | ............. A61K/31/52 |
| 98/57651 | 12/1998 | (WO) | ............. A61K/31/70 |
| 00/44763 | 1/2000 | (WO) | ............. C07H/19/00 |

OTHER PUBLICATIONS

Ali, H., et al., "Methylxanthines Block Antigen–induced Responses in RBL–2H3 Cells Independently of Adenosine Receptors or Cyclic AMP: Evidence for Inhibition of Antigen Binding to IgE", *Journal of Pharmacology and Experimental Therapeutics*, 258, pp. 954–962, (1991).

Carruthers, A.M., et al., "Hypotensive Responses to the Putative Adenosine $A_3$ Receptor Agonist $N^6$–2–(4–Aminophenyl)–Ethyladenosine in the Rat", *Drug Development Research*, 30, pp. 147–152, (1993).

de Moraes, V.L., et al., "Effect of cyclo–oxygenase inhibitors and modulators of cyclic AMP formation on lipopolysaccharide–induced neutrophil infiltration in mouse lung", *British Journal of Pharmacology*, 117, pp. 1792–1796, (1996).

Fozard, J.R., "Adenosine $A_3$ Receptors Mediate Hypotension in the Angiotensin II–supported Circulation of the Pithed Rat", *British Journal of Pharmacology*, 109 (1), pp. 3–5, (1993).

Hartung, H.P., "Immune–Mediated Demyelination", *Annals of Neurology*, 33 (6), pp. 563–567, (Jun. 1993).

Leclerc, G., et al., "Percutaneous Arterials Gene Transfer in a Rabbit Model", *Journal of Clinical Investigation*, 90 (3), pp. 936–944, (1992).

Bruns, R.F., "Adenosine Receptors—Roles and Pharmacology", *Biological Actions of Extracellular ATP*, 603, Annals of The New York Academy of Sciences, pp. 211–226, (1990).

Bruns, R.F., et al., "Characterization of the $A_2$ Adenosine Receptor Labeled by [$^3$H]NECA in Rat Striatal Membranes", *Molecular Pharmacology*, 29, pp. 331–346, (1986).

Fang, G.D., et al., "A New Selective Adenosine $A_{2a}$ Receptor Agonist, Improves Survival in *E. coli* 026:B6 Lipopolysaccharide (LPS)–Induced Experimental Murine Endotoxemia", *Journal of Investigative Medicine*, Abstract No. 797, p. 148A, (2000).

Glover, D.K., et al., "Characterization of a New, Highly Selective Adenosine $A_{2A}$ Receptor Agonist with Potential Use in Pharmacologic Stress Perfusion Imagine", *Circulation*, 100, Abstract, (1999).

Glover, D.K., et al., "Vasodilator Stress Imaging Using New Adenosine $A_{2A}$ Receptor Agonists Administered by Bolus Injection", *J. Am. Coll. Cardiol.*, 35, Abstract, (2000).

(List continued on next page.)

*Primary Examiner*—Dameron L. Jones
(74) *Attorney, Agent, or Firm*—Schwegman, Lundberg, Woessner & Kluth, P.A.

(57) ABSTRACT

A method is provided employing $A_{2A}$ adenosine receptor agonists as vasodilators to detect the presence and assess the severity of coronary artery stenosis.

24 Claims, 3 Drawing Sheets

OTHER PUBLICATIONS

Heller, L.J., et al., "Effect of Adenosine on Histamine Release and Atrioventricular Conduction During Guinea Pig Cardia Anaphylaxis", *Circulation Research*, 62 (6), pp. 1147–1158, (Jun. 1988).

Ito, B.R., et al., "Role of Cardiac Mast Cells In Complement C5a–induced Myocardial Ischemia", *American Journal of Physiology*, 264 (5), Part 2 of Two Parts, pp. H1346–H1354, (May 1993).

Jolly, S.R., et al., "Effects of Lodoxarnide on Ischemic Reperfused Myocardium", *Journal of Cardiovascular Pharmacology*, 4 (3), pp. 441–448, (1982).

Keller, A.M., et al., "Acute Reoxygenation Injury in the Isolated Rat Heart: Role of Resident Cardiac Mast Cells", *Circulation Research*, 63 (6), pp. 1044–1052, (Dec. 1988).

Linden, J., et al., "[$^{125}$I] Aminobenzyladenosine, a New Radioligand with Improved Specific Binding to Adenosine Receptors in Heart", *Circulation Research*, 56 (2), pp. 279–284, (Feb. 1985).

Linden, J., et al., "Adenosine Receptors", *In: Handbook of Receptos and Channels—G Protein Coupled Receptors*, Chapter 2, Edited by S.J. Peroutka, Published by CRC Press, Boca Raton, FL, pp. 29–44, (1994).

Linden, J., et al., "Molecular Cloning and Functional Expression of a Sheep A3 Adenosine Receptor with Widespread Tissue Distribution", *Molecular Pharmacology*, 44 (3), pp. 524–532, (Sep. 1993).

Mahan, L.C., et al., "Cloning and Expression of an $A_1$ Adenosine Receptor from Rat Brain", *Molecular Pharmacology*, 40 (1), pp. 1–7, (Jul. 1991).

Mumby, S.M., et al., "G–protein α–subunit expression, myristoylation, and membrane association in COS cells", *Proceedings of the National Academy of Sciences*, 87 (2), pp. 728–732, (Jan. 1990).

Robeva, A.S., et al., "Molecular Characterization of Recombinant Human Adenosine Receptors", *Drug Development Research*, 39, pp. 243–252, (1996).

Schiffmann, S.N., et al., "Distribution of adenosine $A_2$ receptor mRNA in the human brain", *Neuroscience Letters*, 130, pp. 177–181, (1991).

Ukena, D., et al., "Species Differences in Structure–Activity Relationships of Adenosine Agonists and Xanthine Antagonists at Brain $A_1$ Adenosine Receptors", *FEBS Letters*, 209 (1), pp. 122–128, (Dec. 1986).

van Calker, D., et al., "Adenosine Regulates via Two Different Types of Receptors, the Accumulation of Cyclic AMP in Cultured Brain Cells", *Journal of Neurochemistry*, 33, pp. 999–1005, (1979).

Wan, A.A., et al., "Binding of the Adenosine $A_2$ Receptor Ligand ($^3$H)CGS 21680 to Human and Rat Brain: Evidence for Multiple Affinity Sites", *Journal of Neurochemistry*, pp. 1763–1771, (1990).

Wolff, A.A., et al., "Ventricular Arrhythmias Parallel Cardiac Histamine Efflux After Coronary Artery Occlusion in the Dog", *Agents and Actions*, 25 (3/4), pp. 296–306, (1988).

Andersson, P., et al., "Anti–anaphylactic and anti–inflammatory effects of xanthines in the lung", *Curr. Clin. Pract. Ser.*, , 187–192, (1985).

Berkich, D.A., et al., "Evidence of Regulated Coupling of A1 Adenosine Receptors by Phosphorylation in Zucker Rats.", *American Physiological Society*, 268(4 Pt. 1), E693–E704, (Apr., 1995).

Bhattacharya, S., et al., "Effects of Long–term Treatment With the Allosteric Enhancer, PD81,723, on Chinese Hamster Ovary Cells Expressing Recombinant Human $A_1$ Adenosine Receptors", *Molecular Pharmacology*, 50(1), 104–111, (Jul., 1996).

Bhattacharya, S., et al., "The Allosteric Enhancer, PD 81,723, Stabilizes Human $A_1$ Adenosine Receptor Coupling to G Proteins", *Biochimica Biophysica Acta*, 1265(1), 15–21, (Feb. 1995).

Bridges, A.J., et al., "$N^6$ –[2–(3, 5–Dimethoxyphenyl)–2–(2–Methylphenyl)–Ethyl]Adenosine and Its Uronamide Derivatives. Novel Adenosine Agonists With Both High Affinity and High Selectivity for the Adenosine $A_2$ Receptor", *Journal of Medicinal Chemistry*, 31(7), 1282–1285, (1988).

Buster, B., et al., "The Effect of Adenosine Receptor Agonists on Neutrophil Pleocytosis and Blood–Brain Barrier Pathophysiology in Experimental Bacterial Meningitis", *Abstract of the Interscience Conference on Antimicrobial Agents and Chemotherapy*, 37, 39, (1997).

Cembrzynska, N.M., et al., "Elevated Release of Tumor Necrosis Factor–alpha and Interferon–gamma by Bronchoalveolar Leukocytes From Patients With Bronchial Asthma.", *American Review of Respiratory Disease*, 147(2), 291–295, (1993).

Cothran, D.L., et al., "Ontogeny of Rat Myocardial $A_1$ Adenosine Receptors", *Biol Neonate*, 68(2), 111–118, (1995).

Cristalli, G., et al., "Alkynyl Derivatives of Adenosine an Adenosine–5'–N–ethyluronamide as Selective Agonists at $A_2$ Adenosine Receptors1", *Journal of Medicinal Chemistry*, 35(13), 2363–2368, (1992).

Cronstein, B.N., et al., "Adenosine Modulates the Generation of Superoxide Anion by Stimulated Human Neutrophils Via Interaction With a Specific Cell Surface Receptor", *Annals New York Academy of Science*, 451, 291–314, (1985).

Cronstein, B.N., et al., "Adenosine; A Physiologic Modulator Of Superoxide Anion Generated By Human Neutrophils. Adenosine Acts Via An $A_2$ Receptor On Human Neutrophils", *Journal of Immunology*, 135(2), 1366–1371, (1985).

Cronstein, B.N., et al., "Engagement of Adenosine Receptors Inhibits Hydrogen Peroxide ($H_2O_2$) Release by Activated Human Neutrophils", *Clinical Immunology and Immunopathology*, 42(1), 76–85, (1987).

Cronstein, B.N., et al., "Methotrexate Inhibits Leukocyte Influx Into Inflammatory Sites Via The Adenosine ($A_2$) Receptor", *Clinical Research*, 41(2), 244A, (1993).

Cronstein, B.N., et al., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation*, 85(4), 1150–1157, (1990).

Cronstein, N., et al., "Occupancy Of Adenosine Receptors Raises Cyclic AMP Alone And In Synergy With Occupancy Of Chemoattractant Receptors And Inhibits Membrane Depolarization", *Biochemical Journal* , 252(3), 709–715, (1988).

De La Harpe, J., et al., "Adenosine Regulates the Respiratory Burst of Cytokine –Triggered Human Neutrophils Adherent To Biological Surfaces", *Journal Of Immunology*, 143(2), 596–602, (1989).

Dinarello, C.A., "Interleukin–1 And Tumor Necrosis Factor: Effector Cytokines In Autoimmune Diseases", *Seminars in Immunology*, 4, 133–145, (1992).

Doyle, M.P., et al., "Nucleoside–induced Arteriolar Constriction: a Mast Cell–dependent Response.", *American Journal of Physiology*, H2042–H2050, (May, 1994).

Feoktistov, I., et al., "Adenosine $A_{2b}$ Receptors", *The American Society for Pharmacological and Experimental Therapeutics*, 49(4), 381–402, (1997).

Feoktistov, I., et al., "Role of Adenosine in Asthma", *Drug Development Research*, 39, 333–336, (1996).

Ferrante, A., et al., "Optimal Conditions for Simultaneous Purification of Mononuclear and Polymorphonuclear Leucocytes From Human Blood by the Hypaque–Ficoll Method", *Journal of Immunological Methods*, 36(2), 109, (1980).

Figler, R.A., et al., "Reconstitution of Bovine $A_1$ Adenosine Receptors and G Proteins in Phospholipid Vesicles: βγ–Subunit Composition Influences Guanine Nucleotide Exchange and Agonist Binding", *Biochemistry*, 36(51), 16288–16299, (1997).

Figler, R.A., et al., "Reconstitution of Recombinant Bovine $A_1$ Adenosine Receptors in Sf9 Cell Membranes with Recombitant G Proteins of Defined Composition.", *Molecular Pharmcology*, 50(6), 1587–1595, (Dec. 1996).

Firestein, G.S., et al., "Adenosine Regulating Agents: A Novel Approach to Inflammation and Inflammatory Arthritis", *Clinical Research*, 41(2), 170A, (1993).

Francis, J.E., et al., "Highly Selective Adenosine $A_2$ Receptor Agonists in a Series of N–Alkylated 2–Aminoadenosines", *Journal of Medicinal Chemistry*, 34(8), 2570–2579, (1991).

Gao, Z., et al., "$A_{2B}$ Adenosine and $P2Y_2$ Receptors Stimulate Mitogen–activated Protein Kinase in Human Embryonic Kidney–293 Cells. Cross–talk Between Cyclic AMP and Protein Kinase c Pathways", *Journal of Biological Chemistry*, 274(9), 5972–5980, (Feb. 1999).

Gao, Z., et al., "Purification of $A_1$ Adenosine Receptor–G–protein Complexes: Effects of Receptor Down–regulation and Phosphorylation on Coupling", *Biochemical Journal*, 338(Pt3), 729–736, (Mar., 1999).

Gilchrist, A., et al., "Antagonists of the Receptor–G Protein Interface Block $G_i$–coupled Signal Transduction", *Journal of Biological Chemistry*, 273(24), 14912–14919, (Jun., 1998).

Glover, D.K., et al., "Pharmacological Stress Thallium Scintigraphy With 2–Cyclohexylmethylidenehydrazinoadenosine (WRC–0470) A Novel, Short–Acting Adenosine A2A Receptor Agonist.", *Circulation* 94, 1726–1732, (1996).

Griswold, D.E., et al., "Effects of Selective Phosphodiesterase Type IV Inhibitor, Rolipram, on Fluid and Cellular Phases of Inflammatory Response", *Chemical Abstract*, 119, Abstract No. 173828e, (1993).

Hanlon, W.A., et al., "rTNFα Facilitate Human Polymorphonuclear Leukocyte Adherence to Fibrinogen Matrices With Mobilization of Specific and Tertiary But Not Azurophilic Granule Markers", *Journal of Leukocyte Biology*, 50(1), 43–48, (1991).

Holmes, et al., "Restenosis After Percutaneous Transluminal Coronary Angioplasty (PTCA): A Report From the PTCA Registry of the National Heart, Lung, and Blood Institute", *American Journal of Cardiology*, 53, 77C–81C, (1984).

Hussain, T., et al., "$^{125}$1–APE Binding to Adenosine Receptors in Coronary Artery: Photoaffinity Labeling with $^{125}$1–azidoAPE", *Journal of Pharmacology and Experimental Therapeutics*, 276(1), 284–288, (Jan. 1996).

Hutchison, A.J., et al., "2–(Arylalkylamino)Adenosine–5'–Uronamides: A New Class of Highly Selective Adenosine $A_2$ Receptor Ligands", *Journal of Medicinal Chemistry*, 33(7), 1919–1924, (1990).

Hutchison, A.J., et al., "CGS 21680C, an $A_2$ Selective Adenosine Receptor Agonist With Preferential Hypotensive Activity", *Journal of Pharmacology and Experimental Therapeutics*, 251(1), 47–55, (1989).

Iannone, M.A., et al., "Effects of Adenosine on Human Neutrophil Function and Cyclic AMP Content", *Topics and Perspectives in Adenosine Research*, eds. E. Gerlach et al., Springer–Verlag, Berlin, Proceedings of the 3rd International Symposium on Adenosine, Munich, Jun. 1986, 286–298, (1986).

Imagawa, D.K., et al., "The Role of Tumor Necrosis Factor in Allograft Rejection", *Transplantation*, 51, 57–62, (Jan. 1991).

Jarvis, M.F., et al., "[$^3$H]CGS 21680, A Selective $A_2$ Adenosine Receptor Agonist Directly Labels A2 Receptors in Rat Brain.", *Journal of Pharmacology and Experimental Therapeutics*, 251(3), 888–893, (Aug. 1989).

Kaminuma, et al., "Effect of T–440, a Novel Type IV Phosphodiesterase Inhibitor, on Allergen–Induced Immediate and Late Asthmatic Reaction and Leukocyte Infiltration into the Airways of Guinea Pigs", *International Archives of Allergy& Immunology*, 112(4), 406–411, (1997).

Kennedy, A.P., et al., "Covalent Modification of Transmembrane Span III of the $A_1$ Adenosine Receptor With an antagonist Photoaffinity Probe.", *Molecular Pharmacology*, 50, 789–798, (Oct. 1996).

Kollias–Baker, C., et al., "Allosteric Enhancer PD 81,723 Acts by Novel Mechanism to Potentiate Cardiac Actions of Adenosine", *Circulation Research*, 75(6), 961–971, (Dec. 1994).

Koshiba, M., et al., "Patterns of $A_{2A}$ Extracellular Adenosine Receptor Expression in Different Functional Subsets of Human Peripheral T Cells. Flow Cytometry Studies With Anti–$A_{2A}$ Receptors Monoclonal Antibodies. ", *Molecular Pharmacology*, 55(3), 614–624, (Mar., 1999).

Legrand–Poels, S., et al., "Activation of Human Immunodeficiency Virus Type 1 by Oxidative Stress", *AIDS Research and Human Retroviruses*, 6(12), 1389–1397, (1990).

Lette, J., et al., "Safety of Dipyridamole Testing in 73,806 Patients: The Multicenter Dipyridamole Safety Study", *Journal of Nuclear Cardiology*, 2(1), 3–17, (1995).

Linden, J., "Allosteric Enhancement of Adenosine Receptors", *Purinergic Approaches in Experimental Therapeutics*, Editors: Jacobson, Kenneth A. (Ed) & Jarvis, Michael F (Ed), 85–97, (1997).

Linden, J., "Cloned Adenosine $A_3$ Receptors: Pharmacological Properties, Species Differences and Receptor Functions.", *Trends in Pharmacological Sciences*, 15(8), 298–306, (Aug. 1994).

Linden, J., "Recombinant Techniques as Applied to the Study of $A_1$ Adenosine Receptors", *Adenosine Adenine Nucleotides Molecular Biology Integrative Physiology*, Editors: Belardinelli, Luiz (Ed) & Pelleg, Amir (Ed), 15–19, (1995).

Linden, J., et al., "The Structure and Function of $A_1$ and $A_{2B}$ Adenosine Receptors", *Life Science*, 62(17–18), 1519–1524, (1998).

Luthin, D.R., et al., "Adenosine Receptors", *Biomembranes*, 2B, 321–347, (1996).

Luthin, D.R., et al., "Characterization of Two Affinity States of Adenosine $A_{2a}$ Receptors With a New Radioligand, 2–[2–(4–amino–3–[$^{125}$1]iodophenyl) Ethylamino]Adenosine.", *Molecular Pharmacology*, 47(2), 307–313, (Feb. 1995).

Luthin, D.R., et al., "Comparison of $A_4$ and $A_{2a}$ Binding Sites in Striatum and COS Cells Transfected With Adesosine $A_{2a}$ Receptors.", *Journal of Pharmacology and Experimental Therapeutics*, 272, 511–518, (Feb. 1995).

Luthin, D.R., et al., "Photoaffinity Labeling With 2(–) [2–(4–azido–3(–)[$^{125}$1]–iodophenyl)ethylamino]Adenosine and Autoradiography With 2(–) [2–(4–amino–3(–)[$^{125}$1]iodophenyl)ethylamino]Adenosine of $A_{2a}$ Adenosine Receptor in Rat Brain.", *Journal of Neurochemistry*, 65(5), 2072–2079, (Nov. 1995).

Mannel, D.N., et al., "Tumor Necrosis Factor: A Cytokine Involved in Toxic Effects of Endotoxin", *Reviews of Infectious Diseases*, 9, S602–S606, (1987).

Martin, P.L., et al., "Characterization of 8–(N–methylisopropyl)amino–N$^6$–(5'–andohydroxy– endonorbornyl)–9–methyladenine (WRC–0571), a Highly Potent and Selective, Non–xanthine Antagonist of $A^1$ Adenosine Receptors.", *Journal of Pharmacology and Experimental Therapeutics*, 276(2), 490–499, (Feb. 1996).

Martin, P.L., et al., "Pharmacology of 2–cyclohexylmethylidenehydrazinoadenosine (WRC–0470), a Novel, Short–acting Adenosine $A_{2A}$ Receptor Agonist That Produces Selective Coronary Vasodilation.", *Drug Development Research*, 40(4), 313–324, (1997).

Matherne, G.P., et al., "Transgenic A1 Adenosine Receptor Overexpression Increases Myocardial Resistence to Ischemia", Proceedings of the National Academy of Science, USA, 94, 6541–6546, (Jun., 1997).

Matsuyama, T., et al., "Cytokines and HIV Infection: is AIDS a Tumor Necrosis Factor Disease?", *AIDS*, 5(12), 1405–1417, (1991).

McGarrity, S.T., et al., "Inhibition of Neutrophil Superoxide Anion Generation by Platelet Products: Role of Adenine Nucleotides", *Journal of Leukocyte Biology*, 44(5), 411–421, (1988).

McGarrity, S.T., et al., "Regulation of Human Neutrophil Function by Adenine Nucleotides", *Journal of Immunology*, 142(6), 1986–1994, (1989).

McLaughlin, D.P., et al., "Hemodynamic and Metabolic Correlates of Dipyridamole–induced Myocardial Thallium–201 Perfusion Abnormalities in Mutlivessel Coronary Artery Disease.", *American Journal of Cardiology*, 73(16), 1159–1164, (Jun., 1994).

Merritt, H.R., et al., "Abnormal Q Waves are Common Early in AMI and Do Not Predict Decreased Myocardial Salvage With Thrombolytic Therapy", *Journal of American College of Cardiology*, 895–897, (Feb. 1994).

Mizumura, T., et al., "PD 81,723, an Allosteric Enhancer of the $A_1$ Adenosine Receptor, Lowers the Threshold for Ischemic Preconditioning in Dogs.", *Circulation Research*, 79(3), 415–423, (Sep. 1996).

Molnar–Kimber, K.L., et al., "Modulation of TNFα and IL–1β From Endotoxin–Stimulated Monocytes by Selective PDE Isozyme Inhibitors", *Agents & Actions*, 39, C77–C79, (1993).

Nabel, E.G., et al., "Site–Specific Gene Expression in Vivo by Direct Gene Transfer into the Arterial Wall", *Science*, 249, 1285–1288, (1990).

Newman, K.D., et al., "Adenovirus–mediated Gene Transfer into Normal Rabbit Arteries Results in Prolonged Vascular Cell Activation, Inflammation and Neointimal Hyperplasia", *Journal of Clinical Investigation*, 96(6), 2955–2965, (1995).

Nielson, C.P., et al., "Effects of Adenosine on Polymorphonuclaer Leucocyte Function, Cyclic 3': 5'–adenosine Monophosphate, and Intracellular Calcium", *British Journal of Pharmacology*, 97(3), 882–888, (1989).

Niiya, K., et al., "2–(N'–Alkylidenehydrazino)Adenosines: Potent and Selective Coronary Vasodilators", *Journal of Medicinal Chemistry*, 35(24), 4557–4561, (1992).

Nolte, "Reduction of Postischemic Leukocyte–Endothelium Interaction by Adenosine Via $A_2$ Receptor", *Biological Abstract*, 94(11), Abstract No. 116779, (1992).

O'Regan, M.H., et al., "Adenosine Receptor Agonists Inhibit the Release of γ–Aminobutyric Acid (GABA) From the Ischemic Rat Cerebral Cortex", *Chemical Abstracts*, 117, Abstract No. 104867p, 170, (1992).

Olsson, R.A., et al., "N$^6$ Substituted N–Alkyladenosine–5'–Uronamides: Bifunctional Ligands Having Recognition Groups for A1 and A2 Adenosine Receptors", *Journal of Medicinal Chemistry*, 29(9), 1683–1689, (1986).

Peet, N.P., et al., "Conformationally Restrained, Chiral (Phenylisopropyl)Amino–Substituted Pyrazolo[3,4–d]Pyrimidines and Purines With Selectivity for Adenosine $A_1$ and $A_2$ Receptors", *Journal of Medicinal Chemistry*, 35(17), 3263–3269, (1992).

Pfister, J.R., et al., "Synthesis and Biological Evaluation of the Enantiomers of the Potent and Selective $A_1$– adenosine Antagonist 1,3–dipropyl–8–[2–(5,6–epoxynorbonyl)]–xanthaine", *Journal of Medicinal Chemistry*, 40(12), 1773–1778, (Jun., 1997).

Ranhosky, A., et al., "The Safety of Intravenous Dipyridamole Thallium Myocardial Perfusion Imaging", *Circulation*, 81(4), 1205–1209, (Apr., 1990).

Roberts, P.A., et al., "Inhibition by Adenosine of Reactive Oxygen Metabolite Production by Human Polymorphonuclear Leucocytes", *Biochemical Journal*, 227(2), 669–674, (1985).

Robeva, A.S., et al., "Double Tagging Recombitant $A_1$– and $A_{2A}$–Adenosine Receptors With Hexahistidine and the Flag Epitope. Development of an Efficient Generic Protein Purification Procedure.", *Biochemical Pharmacology*, 51(4), 545–555, (Feb. 1996).

Rosin, D.L., et al., "Immunohistochemical Localization of Adenosine $A_{2A}$ Receptors in the Rat Central Nervous System", *Journal of Comparative. Neurology*, 402(2), 163–186, (Nov. 1998).

Rothe, G.A., et al., "Flow Cytometric Measurement of the Respiratory Burst Activity of Phagocytes Using Dihydrorhodamine 123", *Journal of Immunological Methods*, 138(1), 133–135, (1991).

Sawmiller, D.R., et al., "Effects of Xanthine Amine Congener on Hypoxic Resistence and Venous and Epicardial Adenosine Concentrations.", *Cardiovascular Research*, 28(5), 604–609, (May, 1994).

Schlack, et al., "Adenosine $A_2$–Receptor Activation at Reperfusion reduces Infarct Size and Improves Myocardial Wall Function in Dog Heart", *Biological Abstract*, 96(6), Abstract No. 67801, (1993).

Schrier, D.J., et al., "Effects of Adenosine Agonists on Human Neutrophil Function", *Journal of Immunology*, 137(10), 3284–3289, (1986).

Seekamp, A., et al., "Ischemia—Reperfusion Injury", *Agents and Actions Supplements*, 41, 137–152, (1993).

Sharief, M.K., et al., "Elevated Serum Levels of Tumor Necrosis Factor–α in Guillain–Barre Syndrome", *Annals of Neurology*, 33, 591–596, (Jun. 1993).

Shepherd, R.K., et al., "Adenosine–induced Vasoconstriction in Vivo. Role of the Mast Cell and $A_3$ Adenosine Receptor.", *Circulation Research*, 78(4), 627–634, (Apr., 1996).

Sipka, S., et al., "Adenosine Induced Delay of Expression of AIDS Virus, HIV, in H9T Cells", *Acta. Biochimica et Biophysica Hungarica*, 23(1), 75–82, (1988).

Siragy, H.M., et al., "Sodium Intake Markedly Alters Renal Interstitial Fluid Adenosine", *Hypertension*, 27(3 Pt 1), 404–407, (Mar., 1996).

Smits, P., et al., "Cardiovascular effects of two xanthines and the relation to adenosine antagonism", *Clinical Pharmacology and Therapeutics*, 45(6), 593–599, (1989).

Sullivan, G.W., et al., "Adenosine (ADO) Modulates Endotoxin and TNF–Induced PMN Activation", *Clinical Research*, 41(2), 172A, (1993).

Sullivan, G.W., et al., "Role of $A_{2A}$ Adenosine Receptors in Inflammation", *Drug Development Research*, 45(3/4), 103–112, (1998).

Sullivan, G.W., et al., "The Specific Type IV Phosphodiesterase Inhibitor Rolipram Combined with Adenosine Reduces Tumor Necrosis Factor–α–Primed Neutrophil Oxidative Activity", *International Journal of Immunonopharmacology*, 17(10), 793–803, (1995).

Sullivan, G.W., et al., "Two Methylxanthines, Pentoxifylline (PTX) and Caffeine (CAF) Have Divergent Effects on Tumor Necrosis Factor (TNF)–Primed Human Neutrophil (PMN) Activation", *Clinical Research*, 41(2), 172A, (1993).

Topol, E.J., et al., "Randomised Trial of Coronary Intervention With Antibody Against Platelet IIb/IIIa integrin for Reduction of Clinical Restenosis: Results at Six Months", *The Lencet*, 343(8902), 881–886, (1994).

Tracey, K.J., et al., "Cachectin/Tumor Necrosis Factor Induces Cachexia, Anemia, and Inflammation", *Journal of Experimental Medicine*, 167, 1211–1227, (Mar. 1988).

Tucker, A.L., et al., "$A_1$ Adenosine Receptors. Two Amino Acids are Responsinble for Species Differences in Ligand Recognition", *Journal of Biological Chemistry*, 269(45), 27900–27906, (Nov. 1994).

Ueeda, M., et al., "2– Alkoxyadenosines: Potent and Selective Agonists at the Coronary Artery $A_2$ Adenosine Receptor", *Journal of Medicinal Chemistry*, 34(4), 1334–1339, (1991).

Underwood, D.C., et al., "Inhibition of Antigen–Induced Bronchoconstriction and Eosinophil Infiltration in the Guinea by the Cyclic AMP–Specific Phosphodiesterase Inhibitor, Rolipram", *Chemical Abstracts*, 119(16), Abstract No. 173975a, 67, (1993).

Van Calker, D., et al., "Carbamazepine Distinguishes Between Adenosine Receeotors That Mediate Different Second Messenger Responses", *European Journal of Pharmacology*, 206(4), 285–290, (1991).

Walker, B.A., et al., "Adenosine $A_{2a}$ Receptor Activation Delays Apoptosis in Human Neutrophils", *The American Association of Immunologists*, 2926–2931, (1997).

Yoneyama, F., et al., "Vasodepressor Mechanisms of 2–(1–octynyl) –Adenosine (YT–146), a Selective Adenosine $A_2$ Receptor Agonist, Involve the Opening of Glibenclamide–sensitive $K^+$ Channels", *European Journal of Pharmacology*, 213(1), 199–204, (1992).

Abiru, T., et al., "Nucleosides and Nucleotides. 107. 2–(Cycloalkylalkynyl) adenosines: Adenosine A2 Receptor Agonists with Potent Antihypertensive Effects", *Journal of Medicinal Chemistry*, 35, pp. 2253–2260, (1992).

Baraldi, P.G., et al., "Synthesis and Biological Activity of a New Series of N6–Arylcarbamoyl, 2–(Ar)arlkynyl–6–0arylcarbamoyl, and N6–Carboxamido derivatives of adenosine–5'–N–ethyluronamide as A1 and A3 Adenosine receptor agonists", *J. Med. Chem.*, vol. 41, No. 17, pp. 3174–3185, (1998).

Koshiba, M., et al., "Patterns of A2A Extracellular Adenosine Receptor Expression in Different Functional Subsets of Human Peripheral T Cells", *The FASEB Journal*, Abstract No. 703.38, p. A944, (1999).

Mager, P.P., "Neutal network approaches applied to selective A2a adenosine receptor agonists", *Med. Chem. Res.*, vol. 8, No. 6, pp. 277–290, (1998).

McPherson, J.A., et al., "Effect of Prolonged Adenosine A2A Receptor Activation on Neointimal Formation in the Injured Mouse Carotid Artery", *The FASEB Journal*, Abstract No. 299.2, p. A367, (1999).

Okusa, M.D., et al., "Selective A2A adenosine receptor activation reduces ischemia–reperfusion injury in rat kidney", *Am. J. Physiol.*, 3 (Pt 2), pp. F404–F412, (1999).

INDUCTION OF PHARMACOLOGICAL STRESS WITH ADENOSINE RECEPTOR AGONISTS

The present invention was made with the assistance of U.S. Government funding (NIH Grant ROL HL37942). The U.S. Government has certain rights in this invention.

FIELD OF THE INVENTION

The present invention relates to methods and compositions for carrying out pharmacological stress imaging with certain alkynyladenosine compounds.

BACKGROUND OF THE INVENTION

Pharmacologic stress is increasingly being employed as an alternative to exercise stress in patients undergoing nuclear or echocardiographic imaging for the detection of coronary artery disease. It is frequently induced with adenosine or dipyridamole in patients with suspected coronary artery disease prior to imaging with radiolabeled perfusion tracers such as $^{201}$Tl or $^{99m}$Tc-sestamibi, or by echocardiography. In 1999, it is predicted that 1.7 million patients will be studied using pharmacologic stress imaging in the United States alone. The advantage of pharmacologic vasodilatation over exercise is that pharmacologic stress results in a repeatable level of coronary flow increase which is not dependent upon patient fitness and/or motivation. The sensitivity and specificity for the detection of coronary artery disease is high for both adenosine and dipyridamole stress perfusion imaging, ranging between 85–90%.

A major disadvantage of using adenosine or dipyridamole stress is that there is an unusually high incidence of adverse side effects with both of these vasodilators. In one prospective study of 9,256 patients that underwent adenosine stress radionuclide imaging, 82% experienced adverse side effects (M. D. Cequiera et al., *J. Am. Coll. Cardiol.*, 23, 384 (1994)). The most common side effects were flushing (37%), chest pain (35%), shortness of breath or dyspnea (35%), headache (14%), ECG changes (9%), and A-V conduction block (8%). A similar side effect profile has been reported for dipyridamole. In a study by A. Ranhosky et al. (*Circulation*, 81, 1205 (1990)) with 3,911 patients receiving dipyridamole, 19.7% experienced chest pain, 12% had headaches, and 8% had ST-segment changes on their ECG. In addition to these side effects, a substantial number of patients experience a marked decrease in blood pressure during the administration of these vasodilators. In another 3,715 patients receiving dipyridamole, the mean systolic blood pressure fell by 14 mm Hg with 11% of the patients demonstrating a >20% drop in systolic blood pressure (J. Lette et al., *J. Nucl. Cardiol.*, 2, 3 (1995)).

Whereas the desired coronary vasodilatation is mediated by the stimulation of the adenosine $A_{2A}$ receptor by adenosine, most of the side effects are caused by stimulation of the other three adenosine receptor subtypes: $A_1$, $A_{2B}$, and $A_3$. While a pre-treatment strategy with an adenosine receptor antagonist may reduce some side effects and improve patient comfort and safety, a simpler strategy would be to design a vasodilator that has little or no affinity for the adenosine $A_1$, $A_{2B}$ or $A_3$ receptor subtypes, but that selectively stimulates the $A_{2A}$ receptors. In fact, there has been progressive development of compounds that are more and more potent and/or selective as agonists of $A_{2A}$ adenosine receptors (AR) based on radioligand binding assays and physiological responses. Initially, compounds with little or no selectivity for $A_{2A}$ receptors were developed, such as adenosine itself or 5'-carboxamides of adenosine, such as 5'-N-ethylcarboxamidoadenosine (NECA) (B. N. Cronstein et al., *J. Immnol.*, 135, 1366 (1985)). Later, it was shown that addition of 2-alkylamino substituents increased potency and selectivity, e.g., CV1808 and CGS21680 (M. F. Jarvis et al., *J. Pharmacol. Exp. Ther.*, 251, 888 (1989)). 2-Alkoxy-substituted adenosine derivatives such as WRC-0090 are even more potent and selective as agonists at the coronary artery $A_{2A}$ receptor (M. Ueeda et al., *J. Med. Chem.*, 34, 1334 (1991)).

Olsson et al. (U.S. Pat. No. 5,140,015) disclose certain adenosine $A_2$ receptor agonists of formula:

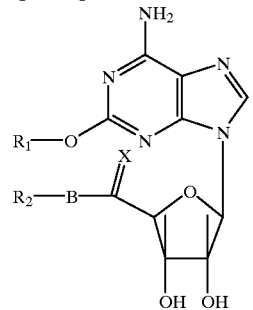

wherein $C(X)BR_2$ can be $CH_2OH$ and $R_1$ can be alkyl- or alkoxyalkyl. The compounds are disclosed to be useful as vasodilators or an antihypertensives.

Linden et al. (U.S. Pat. No. 5,877,180) is based on the discovery that certain inflammatory diseases, such as arthritis and asthma, may be effectively treated by the administration of compounds which are selective agonists of $A_{2A}$ adenosine receptors, preferably in combination with a Type IV phosphodiesterase inhibitor. An embodiment of the Linden et al. invention provides a method for treating inflammatory diseases by administering an effective amount of an $A_{2A}$ adenosine receptor of the following formula:

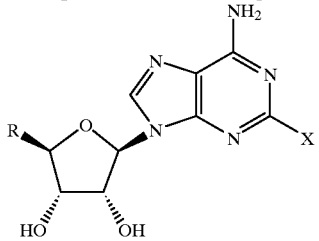

wherein R and X are as described in the patent.

Mohiuddin et al. (U.S. Pat. No. 5,070,877) discloses the use of the relatively nonspecific adenosine analog, 2-chloroadenosine (Cl-Ado), as a pharmacological stressor. However, the Cl-Ado analog is actually a more potent activator of $A_1$ adenosine receptors than of $A_{2A}$ adenosine receptors and, thus, is likely to cause side effects due to activation of $A_1$ receptors on cardiac muscle and other tissues causing effects such as "heart block."

G. Cristalli (U.S. Pat. No. 5,593,975) discloses 2-arylethynyl, 2-cycloalkylethynyl or 2-hydroxyalkylethynyl derivatives, wherein the riboside residue is substituted by carboxy amino, or substituted carboxy amino ($R_3HNC(O)$—). 2-Alkynylpurine derivatives have also been disclosed in Miyasaka et al. (U.S. Pat. No. 4,956,345), wherein the 2-alkynyl group is substituted with ($C_3$–$C_{16}$)alkyl. The '975 compounds are disclosed to be vasodilators and to inhibit platelet aggregation, and thus to be useful as anti-ischeric, anti-atherosclerosis and anti-hypertensive agents.

R. A. Olsson et al. (U.S. Pat. No. 5,278,150) disclose selective adenosine $A_2$ receptor agonists of the formula:

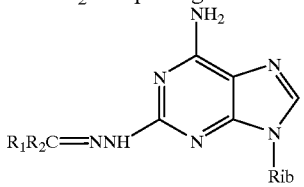

wherein Rib is ribosyl, $R_1$ can be H and $R_2$ can be cycloalkyl. The compounds are disclosed to be useful for treating hypertension, atherosclerosis and as vasodilators.

These 2-alklylhydrazino adenosine derivatives, such as 2-cyclohexyl methylidene hydrainoadenosine (WRC-0474), have also been evaluated as agonists at the coronary artery $A_{2A}$ receptor (K. Niiya et al., *J. Med. Chem.*, 35, 4557 (1992)). WRC-0474 has further been evaluated in the dog model for use in pharmacological stress thallium imaging. See, D. K. Glover et al., *Circulation*, 94, 1726 (1996).

Thus, a continuing need exists for selective $A_2$ adenosine receptor agonists useful for use as pharmacological stressors in stress imaging or in other ventricular function imaging techniques, that preferably have reduced side effects, while being chemically stable and short-acting.

SUMMARY OF THE INVENTION

The present invention comprises compounds and methods of their use for detecting the presence of, and assessing the severity of myocardial perfusion abnormalities, such as due to coronary artery stenosis in a mammal, such as a human or domestic animal. Preferably, the compounds of the invention are used as pharmacological stress-inducing agents or stressors that are useful in pharmacological stress imaging for the detection and assessment of coronary artery stenosis due to coronary artery disease. The preferred compounds of the invention are potent and selective at $A_{2A}$ adenosine receptors, but are also short-acting, so that they are rapidly cleared by the body following the imaging process.

The present compounds comprise a novel class of 2-alkynyladenosine derivatives, substituted at the ethyne position by substituted cycloalkyl moieties. Preferably, the riboside residue is substituted at the 5'-position ("X") by an N-alkyl-(or N-cycloalkyl)aminocarbonyl moiety. Thus, the present invention provides a method for detecting the presence and severity of coronary artery stenosis in a mammal, such as a human subject, comprising (1) administering an amount of one or more compounds of the general formula (I):

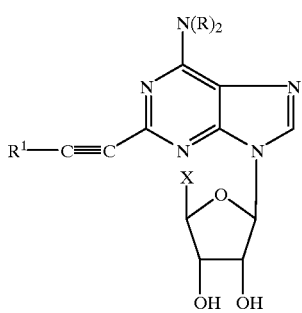

(I)

wherein
(a) each R is individually hydrogen, $C_1$–$C_6$ alkyl, $C_3$–$C_7$ cycloalkyl, phenyl or phenyl($C_1$–$C_3$)-alkyl;
(b) X is —$CH_2OH$, —$CO_2R^2$, —$OC(O)R^2CH_2OC(O)R^2$ or $C(O)NR^3R^4$;
(c) each of $R^2$, $R^3$ and $R^4$ is individually H, $C_{1-6}$-alkyl; $C_{1-6}$-alkyl substituted with 1–3 $C_{1-6}$-alkoxy, $C_{3-7}$-cycloalkyl, $C_{1-6}$-alkylthio, halogen, hydroxy, amino, mono($C_{1-6}$-alkyl)amino, di($C_{1-6}$-alkyl)amino, or $C_{6-10}$-aryl, wherein aryl may be substituted with 1–3 halogen, $C_{1-6}$-alkyl, hydroxy, amino, mono($C_{1-6}$-alkyl)amino, or di($C_{1-6}$-alkyl)amino; $C_{6-10}$-aryl; or $C_{6-10}$-aryl substituted with 1–3 halogen, hydroxy, amino, mono($C_{1-6}$-alkyl)amino, di($C_{1-6}$-alkyl) amino, or $C_{1-6}$-alkyl;

(d) $R^1$ is $(X-(Z)-)_n[(C_3-C_{10})cycloalkyl]-(Z')-$ wherein Z and Z' are individually $(C_1-C_{10})$alkyl, optionally interrupted by 1–3 S or nonperoxide O, or is absent, and n is 1–3; or a pharmaceutically acceptable salt thereof, wherein the amount is effective to provide coronary vasodilation; and (2) performing a technique on said mammal to detect and/or determine the severity of said coronary artery stenosis.

The invention provides a compound of formula I for use in medical diagnostic procedures, preferably for use in detecting the presence of, and assessing the severity of coronary artery stenosis, e.g., due to coronary artery disease in a human subject. The present invention provides the use of a compound of formula I for the manufacture of a pharmacologic vasodilator which can be used with perfusion imaging techniques for diagnosing and assessing the extent of coronary artery stenosis. While the stenosis can be due to coronary artery disease, i.e., atherosclerosis, it can also be due to angioplasty, stent placement or failure and the like.

Preferred perfusion imaging techniques are planar or single photon emission computed tomography (SPECT), gamma camera scintigraphy, positron emission tomography (PET), nuclear magnetic resonance (NMR) imaging, perfusion contrast echocardiography, digital subtraction angiography (DSA) and ultrafast X-ray computed tomography (CINE CT).

The invention also provides a pharmaceutical composition comprising an effective amount of the compound of formula I, or a pharmaceutically acceptable salt thereof, in combination with a pharmaceutically acceptable diluent or carrier. Preferably, the composition is presented as a unit dosage form, and can be adapted for parenteral, e.g., intravenous infusion.

Certain of the compounds of formula I are useful as intermediates in the preparation of other compounds of formula I.

DETAILED DESCRIPTION OF THE INVENTION

Figure 1:
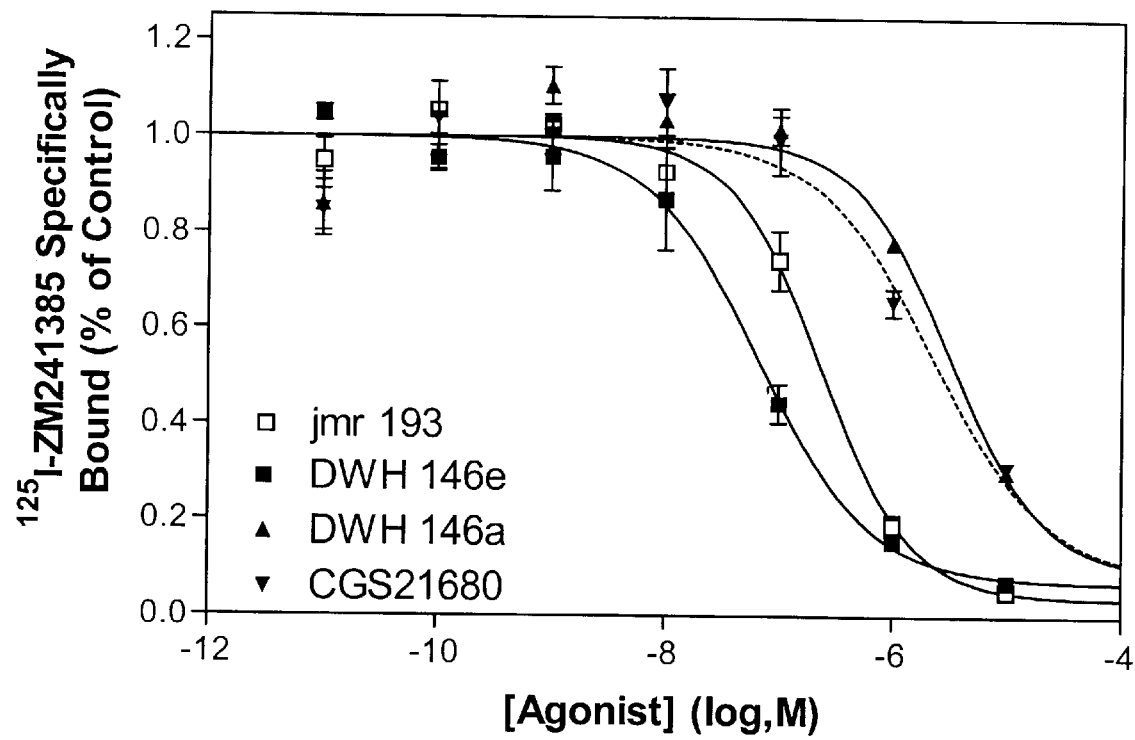
FIG. 1: Competitive binding assay showing the relative potency of three adenosine $A_{2A}$ receptor agonists vs CGS-21680 in recombinant human adenosine receptors.

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$–$C_4$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that the compounds of formula (I) have more than one chiral center and may be isolated in optically active and racemic forms. Preferably, the riboside moiety of formula (I) is derived from D-ribose, i.e., the 3', 4'-hydroxyl groups are alpha to the sugar ring and the 2' and 5' groups is beta (3R, 4S, 2R, 5S). When the two groups on the cyclohexyl group are in the 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Specific and preferred values listed below for radicals, substituents, and ranges, are for illustration only; they do not exclude other defined values or other values within defined ranges for the radicals and substituents.

Specifically, ($C_1$–$C_6$)alkyl can be methyl, ethyl, propyl, isopropyl, butyl, iso-butyl, sec-butyl, pentyl, 3-pentyl, or hexyl. As used herein, the term "cycloalkyl" encompasses (cycloalkyl)alkyl, as well as bicycloalkyl and tricycloalkyl. Thus, ($C_3$–$C_6$)cycloalkyl can be cyclopropyl, norbonyl, adamantyl, cyclobutyl, cyclopentyl, or cyclohexyl; ($C_3$–$C_6$) cycloalkyl($C_1$–$C_6$)alkyl can be cyclopropylmethyl, cyclobutylmethyl, cyclopentylmethyl, cyclohexylmethyl;, 2-cyclopropylethyl, 2-cyclobutylethyl, 2-cyclopentylethyl, or 2-cyclohexylethyl; ($C_1$–$C_6$)alkoxy can be methoxy, ethoxy, propoxy, isopropoxy, butoxy, iso-butoxy, sec-butoxy, pentoxy, 3-pentoxy, or hexyloxy; ($C_2$–$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4hexenyl, or 5-hexenyl; ($C_2$–$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$–$C_6$)alkanoyl can be acetyl, propanoyl or butanoyl; halo($C_1$–$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$–$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$–$C_6$)alkoxycarbonyl ($CO_2R^2$) can be methoxycarbonyl, ethoxycarbonyl, propoxycarbonyl, isopropoxycarbonyl, butoxycarbonyl, pentoxycarbonyl, or hexyloxycarbonyl; ($C_1$–$C_6$)alkylthio can be methylthio, ethylthio, propylthio, isopropylthio, butylthio, isobutylthio, pentylthio, or hexylthio; ($C_2$–$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, puridyl (or its N-oxide), thientyl, pyrimidinyl (or its N-oxide), indolyl, isoquinolyl (or its N-oxide) or quinolyl (or its N-oxide).

A specific value for R is amino, monomethylamino or cyclopropylamino.

A specific value for $R^1$ is carboxy- or ($C_1$–$C_4$) alkoxycarbonyl-cyclohexyl($C_1$–$C_4$)alkyl.

A specific value for $R^2$ is H or ($C_1$–$C_4$)alkyl, i.e., methyl or ethyl.

A specific value for $R^3$ is H, methyl or phenyl.

A specific value for $R^4$ is H, methyl or phenyl.

A specific value for Z is —$CH_2$— or —$CH_2$—$CH_2$—.

A specific value for X is $CO_2R^2$, ($C_2$–$C_5$)alkanoylmethyl or amido.

A specific value for n is 1.

Preferred compounds of formula (I) are those wherein each R is H, X is ethylaminocarbonyl and $R^1$ is 4-carboxycyclohexylmethyl (DWH-146a), $R_1$ is 4-methoxycarbonylcyclohexylmethyl (DWH-146e) or $R^1$ is 4-acetoxymethyl-cyclohexylmethyl (JMR-193). They are depicted below (DWH-146 (acid) and methyl ester (e)) and JMR-193.

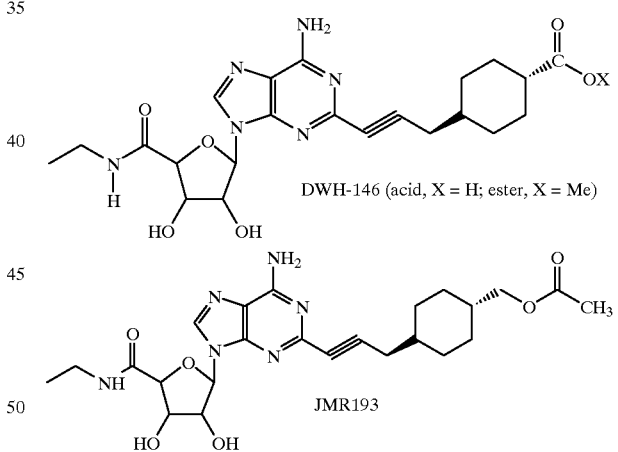

The synthesis of methyl 4[3-(6-amino-9(5-[(ethylamino) carbonyl]-3,4-dihydroxytetrahydro-Z-furanyl-9H-2-purinyl)-2-propynyl]-1-cyclohexanecarboxylate (DWH-146e) was accomplished by the cross coupling of an iodo-adenosine derivative (N-ethyl-1'-deoxy-1'-(amino-2-iodo-9H-purin-9-yl)-β-D-ribofuranuoramide) with methyl 4-(2-propynyl)-1-cyclohexanecarboxylate by utilization of a $Pd^{11}$ catalyst. The synthesis of the iodo-adenosine derivative was accomplished from guanosine. Guanosine is first treated with acetic anhydride, which acetalates the sugar hydroxyls, followed by the chlorination of position 6 with tetramethyl ammonium chloride and phosphorousoxychloride. Iodination of position 2 was accomplished via a modified Sandmeyer reaction, followed by displacement of the 6-Cl and sugar acetates with ammonia. The 2' and 3' hydroxyls were protected as the acetonide and the 5' hydroxyl was iodized to the acid with potassium permanganate. Deprotection of the 2' and 3' acetonide, Fisher esterification of the 5' acid with ethanol and conversion of the resulting ethyl ester to the ethyl amide with ethylamine gave N-ethyl-1'-deoxy-1'-(amino-2-iodo-9H-purin-9-yl)-β-D-ribofuranuoramide.

The acetylene (methyl 4-(2-propynyl)-1-cyclohexanecarboxylate) was synthesized starting from trans-1,4-cyclohexanedimethanol. Initially the trans-diol was monotosylated followed by displacement of the tosylate with an acetylene anion. The hydroxyl of the resulting hydroxyl acetylene species was oxidized to the acid via Jones reagent followed by methylation with (trimethylsilyl) diazomethane to give methyl 4-(2-propynyl)-1-cyclohexanecarboxylate.

The cross-coupling reaction was performed under the following previously reported conditions. To a solution of N,N-dimethylformamide (0.5 mL), acetonitrile (1 mL), triethylamine (0.25 mL), and N-ethyl-1'-deoxy-1'-(amino-2-iodo-9H-purin-9-yl)-β-D-ribofuranuroarnide (25 mg, 0.06 mmol) was added bis(triphenylphosphine)palladium dichloride (1 mg, 2 mol %) and copper(I)iodide (0.06 mg, 0.5 mol %). To the resulting mixture was added methyl 4-(2-propynyl)-1-cyclohexanecarboxylate (54 mg, 0.3 mmol) and the reaction was stirred under $N_2$ atmosphere for 16 hours. The solvent was removed under vacuum and the resulting residue was flash chromatographed in 20% methanol in chloroform ($R_f$=0.45) to give 19 mg (off-white solid, mp 125° C. (decomposed)) of 4[3-(6-amino-9(5-[(ethylamino) carbonyl]-3,4-dihydroxytetrahydro-Z-furanyl)-9H-2-purinyl)-2-propynyl]-1-cyclohexanecarboxylate (DWH-146e).

Other compounds of formula (I) can be prepared by the methodologies disclosed in U.S. Pat. Nos. 5,278,150, 5,140,015, 5,877,180, 5,593,975 and 4,956,345.

Examples of pharmaceutically acceptable salts are organic acid addition salts formed with acids which form a physiological acceptable anion, for example, tosylate, methanesulfonate, malate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or, preferably, parenterally, by intravenous, intramuscular, topical or subcutaneous routes.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The present compounds and compositions containing them are administered as pharmacological stressors and used in conjunction with any one of several noninvasive diagnostic procedures to measure aspects of myocardial perfusion. For example, intravenous adenosine may be used in conjunction with thallium-201 myocardial perfusion imaging to assess the severity of myocardial ischemia. In this case, any one of several different radiopharmaceuticals may be substituted for thallium-201, such as those agents comprising Tc-99m, iodine-123, nitrogen-13, rubidium-82 and oxygen 13. Such agents include technetium 99m labeled radiopharmaceuticals, i.e., technetium 99m-sestamibi, technetium 99m-teboroxime; tetrafosmin and NOET; and iodine 123 labeled radiopharmaceuticals such as I-123-IPPA or BMIPP. Similarly, one of the present compounds may be administered as a pharmacological stressor in conjunction with radionuclide ventriculography to assess the severity of myocardial contractile dysfunction. In this case, radionuclide ventriculographic studies may be first pass or gated equilibrium studies of the right and/or left ventricle. Similarly, a compound of formula (I) may be administered as a pharmacological stressor in conjunction with echocardiography to assess the presence of regional wall motion abnormalities. Similarly, the active compound may be administered as a pharmacological stressor in conjunction with invasive measurements of coronary blood flow such as by intracardiac catheter to assess the functional significance of stenotic coronary vessels.

The method typically involves the administration of one or more compounds of formula (I) by intravenous infusion in doses which are effective to provide coronary artery dilation (approximately 0.25–500, preferably 1–250 mcg/kg/min). However, its use in the invasive setting may involve the intracoronary administration of the drug in bolus doses of 0.5–50 mcg.

Preferred methods comprise the use of a compound of formula (I) as a substitute for exercise in conjunction with myocardial perfusion imaging to detect the presence and/or assess the severity of coronary artery disease in humans wherein myocardial perfusion imaging is performed by any one of several techniques including radiopharmaceutical myocardial perfusion imaging using planar scintigraphy or single photon emission computed tomography (SPECT), positron emission tomograph (PET), nuclear magnetic resonance (NMR) imaging, perfusion contrast echocardiography, digital subtraction angiography (DSA), or ultrafast X-ray computed tomography (CINE CT).

A method is also provided comprising the use of a compound of formula (I) as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide ventriculography.

A method is also provided comprising the use of a compound of formula (I) as a coronary hyperemic agent in conjunction with means for measuring coronary blood flow velocity to assess the vasodilatory capacity (reserve capacity) of coronary arteries in humans wherein coronary blood flow velocity is measured by any one of several techniques including Doppler flow catheter or digital subtraction angiography.

The invention will be further described by reference to the following detailed examples, which are given for illustration of the invention, and are not intended to be limiting thereof.

EXAMPLE 1

Trans-(1-[4-hydroxymethyl)cyclohexyl]methyl)-4-methylbenzenesulfonate (5.2)

Sodium hydride (1.68 g, 70 mmol) was added to a solution of 10 g (70 mmol) [4-(hydroxymethyl)cyclohexyl]methan-1-ol (5.1) in 700 mL of tetrahydrofuran and stirred for 1 hour p-toluenesulfonyl chloride (13.3 g, 70 mmol) was then added and the reaction mixture was refluxed for 5 hours. The reaction was then cooled to 0° C. and slowly quenched with water until there is no more reactive hydride. Once the hydride was quenched, the reaction mixture was diluted with ether (700 mL) and extracted 2 times with 10% aqueous potassium carbonate (700 mL). The organics were dried using sodium sulfate and the solvent was removed under reduced pressure. The product was purified by chromatography on silica gel column eluting with acetone-dichloromethane (5:95) to give 5.2 (35%). $^1$H NMR (300 MHz, CDCl$_3$) δ7.75 (d, J=8.3 Hz, 2H), 7.32 (d, J=8.1 Hz, 2H), 3.79(d, J=6.35 Hz, 2H), 3.39 (d, J=6.35 Hz, 2H), 2.42 (s, 3H), 1.75 (m, 4H), 1.59 (m, 1H), 1.37 (m, 1H), 0.9 (m, 4H). $^{13}$C NMR (300 MHz, CDCl$_3$) δ145.3, 133.4, 130.3, 130.3, 128.3, 128.3, 75.8, 68.5, 40.6, 37.8, 28.9, 28.9, 28.9, 28.9, 22.1.

EXAMPLE 2

(4-prop-2-ynylcyclohexyl)methan-1-ol (5.3)

Lithium acetylide ethylenediamine complex (90%) (6.4 g, 70 mmol) was added very slowly to a solution of 5.2 (3 g, 10 mmol) in 40 mL of dimethylsulfoxide. The reaction mixture was allowed to stir for 5 days and then slowly quenched at 0° C. with water. This mixture was diluted with ether (300 mL) and extracted 3 times with saturated aqueous ammonium chloride (200 mL). The organics were dried with sodium sulfate. The solvent was removed under reduced pressure and the product was purified by chromatography on silica gel column eluting with ethyl acetate-hexanes (20:80) to give 5.3 (85%). $^1$H NMR (300 MHz, CDCl$_3$) δ3.41 (d, J=6.5 Hz, 2H), 2.07 (dd, J=2.5, 6.5 Hz, 2H), 1.96-1.75 (m, 5H), 1.41 (m, 2H), 0.095 (m, 4). $^{13}$C NMR (300 MHz, CDCl$_3$) δ83.8, 69.6, 68.9, 40.7, 37.7, 32.3, 32.3, 29.6, 29.6, 26.5.

EXAMPLE 3

4-prop-2-ynylcyclohexanecarboxylic acid (5.4)

A solution of chromium trioxide (1.1 g, 11 mmol) in 1.5 M sulfuric acid (40 mL, 27 mmol) was maintained at 0° C. while 5.3 (0.46 g, 3 mmol) in 80 mL of acetone was added over 2 hours. The reaction was then stirred for an additional 2 hours at room temperature. The reaction mixture was diluted with ether (200 mL) and extracted 2 times with water. The organics were dried with sodium sulfate. The solvent was removed under reduced pressure and the product was purified by chromatography on silica gel column eluting with acetone-dichloromethane (70:30) to give 5.4 (75%). $^1$H NMR (300 MHz, CDCl$_3$) δ2.24 (dt, J=3.66, 12.1 Hz, 1H), 2.10 (dd, J=2.7, 6.5 Hz, 2H), 2.04-1.89 (m, 5H), 1.76 (d, J=2.3 Hz, 1H), 1.43 (dq, J=3.28, 13.1 Hz, 2H), 1.03 (dq, J=3.28, 13.1 Hz, 2H). $^{13}$C NMR (300 MHz, CDCl$_3$) δ183.2, 83.3, 69.9, 43.4, 36.7, 31.8, 28.9, 26.3.

EXAMPLE 4

Methyl 4-prop-2-ynylcyclohexanecarboxylate (5.5)

(Trimethylsilyl)diazomethane (2.0 M) solution in hexanes (1 mL, 2 mmol) was added to a solution of 5.4 (0.34 g, 2 mmol) in 15 mL of methanol:dichloromethane (3:7). The solvents were removed under reduced pressure resulting in 100% conversion of starting material to product. $^1$H NMR (300 MHz, CDCl$_3$) δ2.24 (dt, J=3.66, 12.1 Hz, 1H), 2.10 (dd, J=2.7, 6.5 Hz, 2H), 2.06 (dd, J=1.54, 6.54 Hz, 1H), 2.00-1.89 (m, 3H), 1.76 (d, J=2.3 Hz, 1H), 1.43 (dq, J=3.28, 13.1 Hz, 2H), 1.03 (dq, J=3.28, 13.1 Hz, 2H). $^{13}$C NMR (300 MHz, CDCl$_3$) δ176.8, 83.3, 69.8, 51.9, 43.4, 36.7, 31.9, 29.2, 26.3.

EXAMPLE 5

[(2R,3R,4R,5R)-3,4-diacetyloxy-5-(2-amino-6-oxohyropurin-9-yl)oxolan-2-yl]methyl acetate (6.2)

A suspension of 113 g (0.4 mol) of dry guanosine (6.1), acetic anhydride (240 mL, 2.5 mol), dry pyridine (120 mL) and dry DMF (320 mL) was heated for 3.75 hours at 75° C. without allowing the temperature to exceed 80° C. The clear solution was then transferred to a 3 L Erlenmyer flask and filled with 2-propanol. Upon cooling the solution to room temperature crystallization was initiated and allowed to proceed at 4° C. overnight. The white solid filtrate was filtered, washed with 2-propanol and recrystallized from 2-propanol to give 6.2 (96%). $^1$H NMR (300 Mhz, CDCl$_3$) δ8.20 (s, 1H, H-8), 6.17 (d, J=5.41 Hz, 1H, H-1') 5.75 (t, J=5.39 Hz, 1H, H-2'), 5.56 (t, J=5.0, H-3'), 4.41 (m, 3H, H-4',5'), 2.14 (s, 3H, Ac), 2.11 (s, 3H, Ac), 2.10 (s, 3H, Ac). $^{13}$C NMR (300 MHz, CD$_3$OD) δ171.0, 170.3, 1702, 157.7, 154.8, 152.4, 136.7, 117.7, 85.5, 80.4, 73.0, 71.3, 64.0, 31.3, 21.2, 21.0.

EXAMPLE 6

[(2R,3R,4R,5R)-3,4-diacetyloxy-5-(2-amino-6-chloropurin-9-yl)oxolan-2-yl]methyl acetate (6.3)

To a 1000 mL flask was added 80 g (0.195 mol) [(2R,3R,4R,5R)-3-4-diacetyloxy-5-(2-amino-6-oxohyropurin-9-yl)oxolan-2-yl]methyl acetate (6.2), tetramethylammonium chloride (44 g, 0.4 mol), anhydrous acetonitrile (400 mL) and N,N-dimethlaniline (25 mL). The flask was placed in an ice salt bath and cooled to 2° C. To this solution was added dropwise $POCl_3$ (107 mL 1.15 mol) at a rate that maintained the temperature below 5° C. (45 minutes). The flask was then removed from the ice bath, outfitted with a condenser, placed in an oil bath and allowed to reflux for 10 minutes whereas the solution changed to a red/brown color. The solvent was then removed under reduced pressure to yield an oily residue which was transferred to a beaker containing 1000 g of ice and 400 mL of $CHCl_3$ and allowed to stir for 1.5 hours to decompose any remaining $POCl_3$. The organic phase was then removed and the aqueous phase extracted with 3×50 mL of $CHCl_3$ and pooled with the organic phase. The pooled organic was then back extracted with 50 mL of water followed by stirring with 200 mL of saturated $NaHCO_3$. The organic was further extracted with $NaHCO_3$ until the aqueous extract was neutral (2×). The organic was finally extracted with brine and then dried over $MgSO_4$ for 16 hours. To the solution was added 800 mL of 2-propanol after which the solution was concentrated under reduced pressure. To the oily solid was added 200 mL of 2-propanol and the solution was refrigerated overnight. The crystalline product was filtered, washed, and allowed to dry overnight to give 6.3 (77%). $^1$H NMR (300 MHz, $CD_3OD$) δ8.31 (s, 1H, H-8), 7.00 (s, 2H, $NH_2$) 6.06 (d, J=5.8 Hz, 1H, H-1'), 5.83 (t, J=6.16 Hz, 1H, H-2'), 5.67 (m 1H, H-3'), 4.29 (m, 3H, H-4',5'), 2.07 (s, 3H, Ac), 1.99 (s, 3H, Ac), 1.98 (s, 3H, Ac). $^{13}$C NMR (300 MHz, $CD_3OD$) δ171.0, 170.4, 170.2, 160.8, 154.6, 150.8, 142.2, 124.5, 85.8, 80.6, 72.8, 71.2, 63.9, 21.4, 21.3, 21.1.

EXAMPLE 7

[(2R,3R,4R,5R)-3,4-diacetyloxy-5-(6-chloro-2-iodopurin-9-yl)oxolan-2-yl]methyl acetate (6.4)

Isoamyl nitrite (5 mL, 37 mmol) was added to a mixture of 5.12 g (12 mmol) [(2R,3R,4R,5R)-3-4-diacetyloxy-5-(2-amino-6-chloropurin-9-yl)oxolan-2-yl]methyl acetate (6.3), $I_2$ (3.04 g, 12 mmol), $CH_2I_2$ (10 mL, 124 mmol), and CuI (2.4 g, 12.6 mmol) in THF (60 mL). The mixture was heated under reflux for 45 minutes and then allowed to cool to room temperature. To this solution was added 100 ml of sat. $Na_2S_2O_3$ which removed the reddish color due to iodine. The aqueous was extracted 3× with chloroform, which was pooled, dried over $MgSO_4$, and concentrated under reduced pressure. The product was then purified over a silica gel column using $CHCl_3$-MeOH (98:2) to collect [(2R,3R,4R,5R)-3,4-diacetyloxy-5-(6-chloro-2-iodopurin-9-yl)oxolan-2-yl]methyl acetate (6.4) (80% crystallized from EtOH). $^1$H NMR (300 MHz, $CDCl_3$) δ8.20 (s, 1H H-8), 6.17 (d, J=5.41 Hz, 1H, H-1'), 5.75 (t, J=5.39 Hz, 1H, H-2'), 5.56 (t, J=5.40 Hz, 1H, H-3'), 4.38 (m, 3H, H-4',5'), 2.14 (s, 1H, Ac), 2.11 (s, 1H, Ac), 2.10 (s, 1H, Ac).

EXAMPLE 8

(4S,2R,3R,5R)-2-(6-amino-2-iodopurin-9-yl)-5-(hydroxymethyl)oxolane-3,4-diol (6.5)

To a flask containing 6.0 g (11.1 mmol) [(2R,3R,4R,5R)-3,4-diacetyloxy-5-(6-chloro-2-iodopurin-9-yl)oxolan-2-yl] methyl acetate (6.4) was added 100 ml of liquid $NH_3$ at −78° C. and the solution was allowed to stir for 6 hours. After which time it was allowed to come to r.t. overnight with concurrent evaporation of the $NH_3$ to yield a brown oil. The product was crystallized from hot isopropanol to give 6.5 (80%), m.p. 143–145° C., r.f.=0.6 in 20% $MeOH/CHCl_3$. $^1$H NMR (300 MHz, DMSO-$d_6$) δ8.24 (s, 1H), 7.68 (s, 2H), 5.75 (d, J=6.16, 1H), 5.42 (d, J=5.40 Hz, 1H), 5.16 (d, J=4.62 Hz, 1H), 499 (t, J=5.39 Hz, 1H), 4.67 (d, J=4.81 Hz, 1H), 4.06 (d, J=3.37 Hz, 1H), 3.89 (m, 1H), 3.54 (m, 2H).

EXAMPLE 9

[(1R,2R,4R,5R)-4-(6-amino-2-iodopurin-9-yl)-7-7-dimethyl-3,6,8-trioxabicyclo[3.3.0]oct-2-yl]methan-1-ol (6.6)

To a solution of 2.0 g (5.08 mmol) (4S,2R,3R,5R)-2-(6-amino-2-iodopurin-9-yl)-5(hydroxymethyl)oxolane-3,4-diol (6.6) in 100 mL acetone was added 9.6 g of p-toluenesulfonic acid and 5 ml of dimethoxypropane. The reaction was stirred at room temperature for 1 hour at which time 15 g of $NaHCO_3$ and then stirred for an additional 3 hours. the residue was filtered and washed 2× with EtOAc. The filtrate was then concentrated under reduced pressure. The residue was chromatographed on a silica gel column with MeOH-$CHCl_3$ (1:99) to give 6.6 (72%) as a solid, m.p. 185–187° C. $^1$H NMR (300 MHz, DMSO-$d_6$) δ8.22 (s, 1H, H-8), 7.69 (s, 2H), $NH_2$), 6.00 (d, J=2.70 Hz, 1H, H-1'), 5.21 (m, 1H, H-2'), 5.07 (bs, 1H, OH), 4.88 (m, 1H, H-3'), 4.13 (m, 1H, H-4'), 3.47 (m, 2H, H-5'), 1.49 and 1.28 (s, 3H, $C(CH_3)_2$).

EXAMPLE 10

(2S,1R,4R,5R)-4-(6-amino-2-iodopurin-9-yl)-7,7-dimethyl-3,6,8-trioxabicyclo[3.3.0]octane-2-carboxylic acid (6.7)

To a stiffed solution of 1.6 g (3.7 mmol) of [(1R,2R,4R,5R)-4-(6-amino-2-iodopurin-9-yl)-7,7-dimethyl-3,6,8-trioxabicyclo[3.3.0]oct-2-yl]methan-1-ol (6.6) in 200 mL of $H_2O$ was added 0.60 g of KOH and, dropwise, a solution of 1.70 g (10.8 ml) of $KMnO_4$ in 50 mL of $H_2O$. The mixture was set aside in the dark at room temperature for 225 hours. The reaction mixture was then cooled to 5–10° C. and decolorized by a solution of 4 mL of 30% $H_2O_2$ in 16 mL of water, while the temperature was maintained under 10° C. using an ice-salt bath. The mixture was filtered through Celite and the filtrate was concentrated under reduced pressure to about 10 mL and then acidified to pH 4 with 2N HCl. The resulting precipitate was filtered off and washed with ether to yield 6.7 (70%) after drying as a white solid, m.p. 187–190° C. $^1$H NMR (300 MHz, DMSO-$d_6$) δ8.11 (s, 1H, H-8), 7.62 (s, 2H, $NH_2$), 7.46 (s, 1H, COOH), 6.22 (s, 1H, H-1'), 5.42 (d, J=5.71 Hz, 1H, H-2'), 5.34 (d, J=6.16 Hz, 1H, H-3'), 4.63 (s, 1H, H-4'), 1.46 and 1.30 (s, 3H, $C(CH_3)_2$).

EXAMPLE 11

(2S,3S,4R,5R)-5-(6-amino-2-iodopurin-9-yl)-3,4-dihydroxyoxolane-2-carboxylic acid (6.8)

A solution of 1.72 g (3.85 mmol) of (2S,1R,4R,5R)-4-(6-amino-2-iodopurin-9-yl)-7,7-dimethyl-3,6,8-trioxabicyclo[3.3.0]octane-2-carboxylic acid (6.7) in 80 mL of 50% HCOOH was stirred at 80° C. for 1.5 hours. The reaction mixture was evaporated under reduced pressure, dissolved in $H_2O$, and the solution was evaporated again. This process was repeated until there was no odor of formic acid in the residue. Recrystallization from water yielded 1.33 g (85%) 6.8 as a white solid, m.p. 221–223° C. dec. $^1$H NMR (300 MHz, DMSO-d$_6$) δ8.31 (s, 1H, H-8), 7.68 (s, 2H, NH$_2$), 5.90 (d, J=6.55 Hz, 1H, H-1'), 4.42 (m, 1H, H-2'), 4.35 (d, J=2.31 Hz, 1H, H-4'), 4.22 (m, 1H, H-3').

EXAMPLE 12

[(2S,3S,4R,5R)-5-(6-amino-2-iodopurin-9-yl)-3,4-dihydroxyoxolan-2-yl]-N-ethylcarboxamide (6.9)

To a cooled (5° C.) and stirred solution of 1.29 g (3.17 mmol) of (2S,3S,4R,5R)-5-(6-aminno-2-iodopurin-9-yl)-3,4-dihydroxyoxolane-2-carboxylic acid (6.8) in 150 mL of absolute ethanol was added dropwise 1.15 mL of ice-cooled SOCl$_2$. The mixture was stirred at room temperature overnight and then brought to pH 8 with saturated aqueous NaHCO$_3$. The mixture was filtered, and then the filtrate was concentrated under reduced pressure to yield a white solid which was dried and then redissolved in 20 mL of dry ethylamine at –20° C. for 3 hours and then at room temperature overnight. The reaction mixture was diluted with absolute ethanol, and the precipitated product was filtered off and washed with dry ether to give 530 mg (72%) of 6.9 as a pure solid, m.p. 232–234° C. $^1$H NMR (300 MHz, DMSO-d$_6$) δ8.34 (s, 1H, H-8), 8.12 (t, 1H, NH), 7.73 (s, 2H, NH$_2$), 5.85, (d, J=6.93 Hz, 1H, H-1'), 4.54 (m, 1H, H-2'), 4.25 (d, J=1.92 Hz, 1H, H-4'), 4.13 (m, 1H, H-3'), 3.28 (m, 2H, CH$_2$CH$_3$), 1.00 (t, J=7.2 Hz, 3H, CH$_2$CH$_3$).

EXAMPLE 13

Methyl-4-(3-{9-[(4S,5S,2R,3R)-5-(N-ethylcarbamoyl)-3,4-dihydroxyoxolan-2-yl]-6-aminopurin-2-yl}prop-2-ynyl)cyclohexane-carboxylate (DWH-146e)

To a degassed solution of 25 mg (0.063 mmol) of [(2S,3S,4R,5R)-5-(6-amino-2-iodopurin-9-yl)-3,4-dihydroxyoxolan-2-yl]-N-ethylcarboxamide (6.9), 16.9 mg (0.094 mmol) (5.5), and 0.75 mg CuI in 5 mL each of TEA and acetonitrile was added 15 mg of Pd(PPh$_3$)$_4$. The solution was stirred for 24 hours at 70° C. after which time the solution was filtered through celite and chromatographed on silica gel with MeOH-CHCl$_3$ (5:95) to give DWH-146e (24%).

EXAMPLE 14

(4-prop-2-ynylcyclohexyl)methyl acetate (5.6)

Acetic anhydride (0.92 mL, 8.25 mmol) and pyridine (0.2 mL, 2.5 mmol) were added to a solution of 5.3 (250 mg, 1.65 mmol) in 25 mL ether. The reaction was allowed to stir at ambient temperature for 24 h. Water was added to the reaction and the organic was further extracted with 10% NaHCO$_3$. The organic layer was dried with MgSO$_4$ and evaporated. The residue was chromatographed on silica gel with EtOAc-Hexanes (5:95) to yield 5.6 (47%).

EXAMPLE 15

[4-(3-{9[(4S,5S,2R,3R)-5-(N-ethylcarbamoyl)-3,4-dihydroxyoxolan-2-yl]-6-aminopurin-2-yl}prop-2-ynyl)cyclohexyl]methyl acetate (JMR193)

To a degassed solution of 125 mg (0.29 mmol) of [(2S,3S,4R,5R)-5-(6amino-2-iodopurin-9-yl)-3,4-dihydroxyoxolan-2-yl]-N-ethylcarboxamide (6.9), 150 mg (0.77 mmol) (5.6), and 1.0 mg CuI in 1.3 mL of TEA and 4 mL DMF was added 25 mg of Pd(PPh$_3$)$_4$. The solution was stirred for 72 h at 60° C. after which time the solution was filtered through celite and chromatographed on silica gel with MeOH-CHCl$_3$ (5:95) to give JMR193 (10%).

EXAMPLE 16

Radioligand Binding Studies

Binding to A$_{2A}$ receptors was evaluated with the radioligand $^{125}$I-ZM241385. FIG. 1 depicts the competition by selective agonists for binding to recombinant human A$_{2A}$ adenosine receptors. DWH-146e is highly selective for the recombinant human A$_{2A}$ (hA2A) subtype. Selectivity for the A$_3$ receptor (not shown) is less impressive, but still about 50-fold. DWH-146e is about 5 and 50 times more potent than WRC0470 and CGS21680, respectively (FIG. 1). An unexpected and interesting finding is that the ester, DWH-146e also is about 50 times more potent than the acid, DWH-146a (FIG. 1).

EXAMPLE 17

Effect of Different Doses of JMR-193e on Coronary Flow and Arterial Pressure in a Canine Model All experiments were performed on fasting adult mongrel dogs anesthetized with pentobarbital sodium (30 mg/kg IV). The animals were intubated and mechanically ventilated (Harvard Apparatus) with room air with a positive end-expiratory pressure of 4 cm H$_2$O. Arterial blood gases were monitored (Model ABL5, Radiometer) and appropriate adjustments were made to maintain pH and blood gases within the normal physiologic range. The left femoral vein was cannulated with an 8F catheter for the administration of fluids and additional anesthesia as required. Both femoral arteries were cannulated with 8F catheters and used for microsphere reference blood withdrawal. An additional 7F catheter was placed in the right femoral artery for monitoring systemic arterial pressure. A 7F Millar high fidelity pressure catheter was inserted into the left ventricle through an 8F sheath in the left carotid artery.

A thoracotomy was performed at the level of the fifth intercostal space and the heart suspended in a pericardial cradle. A cut-down was performed on the left side of the neck, and a Millar pressure catheter advanced through the carotid artery until its tip rested inside the left ventricle. The first derivative of LV pressure (dP/dt) was obtained by electronic differentiation. A flared polyethylene tube was placed in the left a trial appendage for pressure measurement and for injection of microspheres. A snare ligature was loosely placed on a proximal portion of the left anterior descending coronary artery (LAD). Ultrasonic flow probes (T206, Transonic Systems, Inc.) were placed on a more distal portion of the LAD and on the left circumflex coronary artery (LCX). For both protocols, ECG lead II, arterial and left a trial pressures, LAD and LCX flows, and LV pressure and its first derivative were continuously monitored and recorded on a 16-channel thermal array stripchart recorder (model K2G, Astromed, Inc.). In addition to the analog recording, all of the physiologic signals were digitized and stored on an optical disk for subsequent analysis and archival purposes.

Figure 2:
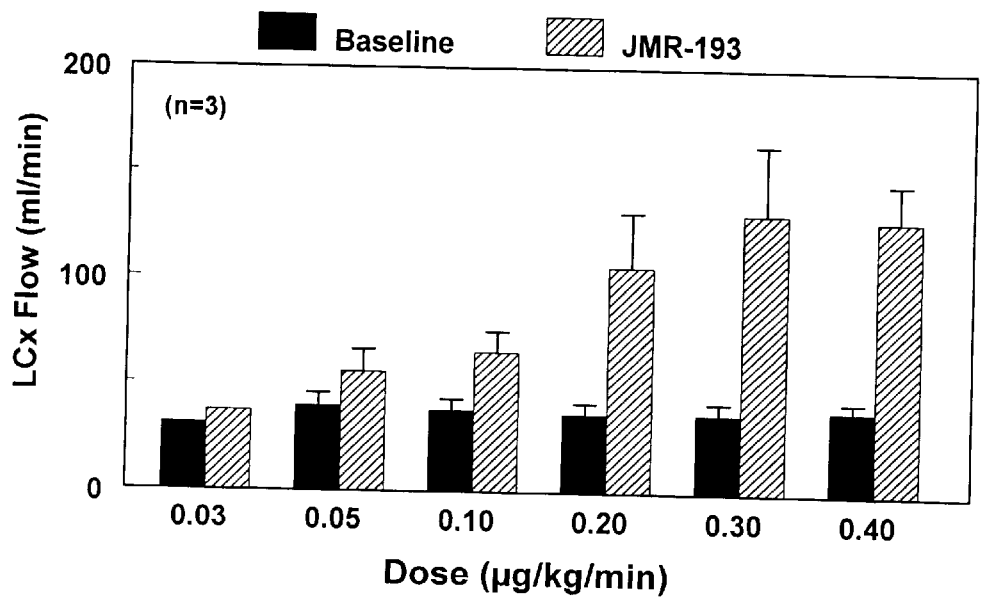
FIG. 2: Left circumflex (LCx) coronary flow response to varying doses of JMR-193 administered by i.v. infusion over 10 minutes.
Figure 3:
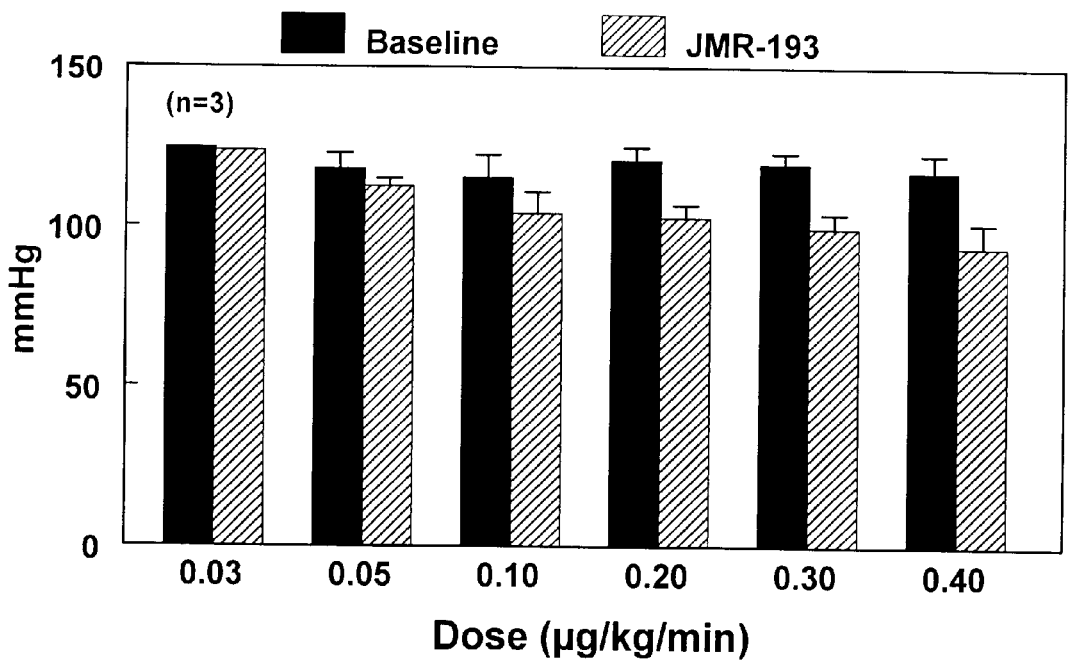
FIG. 3: Mean arterial pressure response to varying doses of JMR-193 administered by i.v. infusion over 10 min.

Following the surgical preparation, three dogs were given varying doses of JMR-193e either by 10 min. i.v. infusion or by bolus administration and the hemodynamic responses were compared against i.v. adenosine (ADO) (250 μg/kg/min×3 min). As shown in FIG. 2, JMR-193e increased LCX coronary flow in a dose-dependent manner from 42 ml/min at baseline to 66, 75, 124, 153, and 140 ml/min at 0.05, 0.1, 0.2, 0.3, and 0.4 μg/kg/min×10 min, respectively. The maximal flow increase occurred at the 0.3 μg/kg/min dose without significant hypotension (117 to 103 mm Hg) as shown in FIG. 3. At the highest dose, maximal flow was attenuated by a mild decrease in arterial pressure (112 to 96 mg Hg). In comparison, ADO increased LCX flow to 139 ml/min but produced a marked drop in arterial pressure from 109 to 80 mm Hg After terminating the JMR-193e infusion, hemodynamics returned to baseline with a pharmacodynamic $t_{1/2}$=12±2 min.

Figure 4:
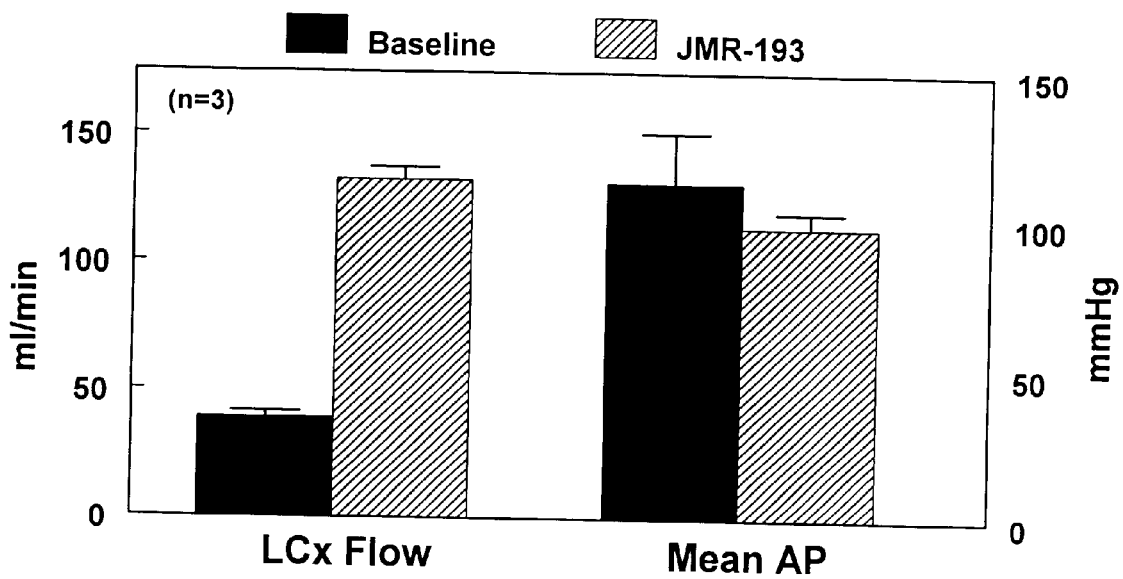
FIG. 4: Peak coronary flow and mean arterial pressure responses to a bolus injection of JMR-193 (0.3 µg/kg).
Figure 5:
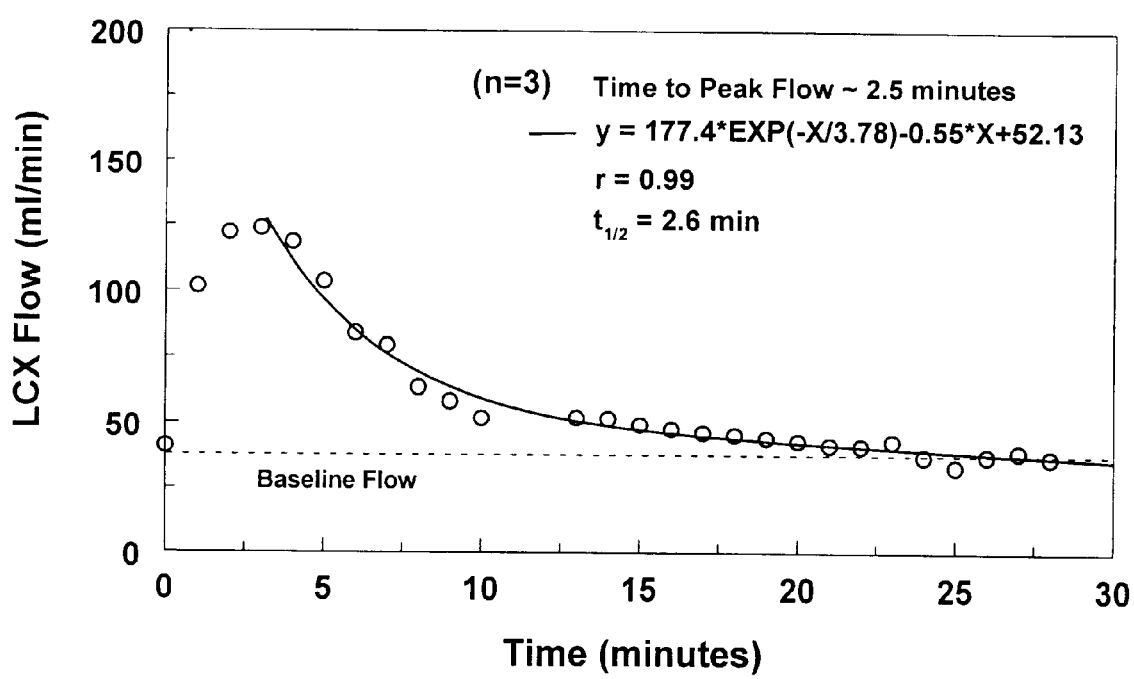
FIG. 5: Pharmacodynamic half-life of a bolus injection of JMR-193 (0.3 µg/kg).

With bolus administration (0.3 μg/kg), JMR-193e increased LCX flow from 41 to 140 ml/min with a minimal decrease in arterial pressure (111 to 100 mm Hg) (FIG. 4). Maximal LCX flow occurred 2.3 min post-injection and flow remained elevated more than 2× normal for 3–4 min (FIG. 4). This extended flow response following bolus administration should make JMR-193e well-suited for clinical imaging protocols. In conclusion, these data show that JMR-193e is useful as a pharmacologic stressor with myocardial perfusion imaging.

EXAMPLE 18

Use of DWH-146e in Pharmacologic Stress Perfusion Imaging

The canine surgical preparation of Example 15 was employed. Following a 15 minute baseline stabilization period, the LAD snare occluder was tightened to produce a critical LAD stenosis. A critical stenosis was defined as one that produced no change in resting coronary flow, however coronary flow reserve was completely abolished. Fifteen minutes later, an i.v. infusion of DWH-146e (0.3 μg/kg/min) was begun and continued for 5 minutes at which time LCX coronary flow was maximal. $^{99m}$Tc-N-NOET (Bis(n-ethyl dithiocarbamato)nitrido $^{99m}$Tc(V)), myocardial perfusion imaging agent with excellent flow-extraction properties, was then injected intravenously (8 mCi). Five minutes later, an in vivo image was acquired and the animal was then immediately killed to prevent $^{99m}$Tc-N-NOET redistribution. The heart was removed and sliced into 4 rings from apex to base. The heart slices were placed on a cardboard sheet, covered with plastic wrap, and ex vivo imaging of the heart slices was performed directly on the collimator of a conventional planar gamma camera.

Image background subtraction was performed on the in vivo image using standard nuclear medicine software developed for this purpose. Defect magnitude was expressed as an LAD/LCX count ratio between counts in LAD and LCX regions of interest drawn on the in vivo and ex vivo heart images. The hemodynamic parameters are summarized in Table 1:

TABLE 1

Hemodynamic Parameters

| | Baseline | Stenosis | Peak DWH-146 |
|---|---|---|---|
| Mean Arterial Pressure (mm Hg) | 100 | 103 | 105 |
| Heart Rate (BPM) | 109 | 123 | 143 |
| LAD Coronary Flow (ml/min) | 39 | 37 | 42 |
| LCX Coronary Flow (ml/min) | 39 | 38 | 185 |
| dP/dt (mm Hg · sec−1) | 2906 | 2713 | 2606 |

As can be seen, DWH-146e infusion increased coronary flow nearly 5-fold in the normal LCX coronary artery. However, coronary flow in the LAD coronary artery remained constant due to the presence of the flow-limiting coronary stenosis. Thus, there was a 5:1 disparity in coronary flow at the time when $^{99m}$Tc-N-NOET was injected. Importantly, there was no change in mean arterial pressure with DWH-146e infusion.

The in vivo and ex vivo images from this dog showed readily detectable large anteroseptal perfusion defects. The $^{99m}$Tc-N-NOET defect count ratio was identical on both the in vivo and ex vivo images and was similar to what is observed using adenosine and $^{201}$Thallium imaging in dogs with the same degree of coronary stenosis.

The excellent coronary flow disparity created by this new class of adenosine $A_{2A}$ receptor subtype agonist was readily detectable using pharmacologic stress perfusion imaging. The nearly 5-fold increase in coronary flow without the development of hypotension indicates that the present compounds would be useful as vasodilators for clinical imaging.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to diagnose coronary artery stenosis in a mammal comprising:
   (a) parenterally administering to said mammal an amount of a compound of formula (I):

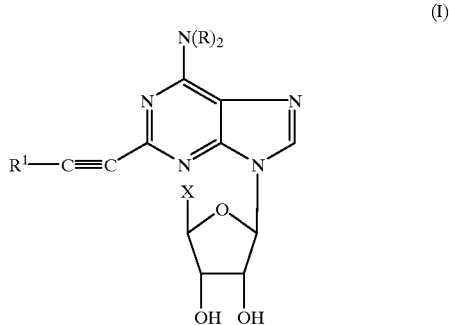

(I)

wherein (a) each R is individually hydrogen, $C_1$–$C_6$ alkyl, $C_3$–$C_7$ cycloalkyl, phenyl or phenyl($C_1$–$C_3$)-alkyl;
(b) X is —$CH_2OH$, —$CO_2R^2$, —$OC(O)R^2$, —$CH_2OC(O)R^2$ or $C(O)NR^3R^4$;
(c) each of $R^2$, $R^3$ and $R^4$ is individually H, $C_{1-6}$-alkyl; $C_{1-6}$-alkyl substituted with 1–3 $C_{1-6}$-alkoxy, $C_3$–$C_7$-cycloalkyl, $C_{1-6}$-alkylthio, halogen hydroxy, amino, mono($C_{1-6}$-alkyl)amino, di($C_{1-6}$-alkyl)amino, or $C_{6-10}$-aryl, wherein aryl may be substituted with 1–3 halogen, $C_{1-6}$-alkyl, hydroxy, amino, mono($C_{1-6}$-alkyl)amino, or di($C_{1-6}$-alkyl)amino; $C_{6-10}$-aryl; or $C_{6-10}$-aryl substituted with 1–3 halogen, hydroxy, amino, mono($C_{1-6}$-alkyl)amino, di($C_{1-6}$-alkyl)amino or $C_{1-6}$-alkyl;
(d) each of $R^3$ and $R^4$ is individually hydrogen, $C_{3-7}$-cycloalkyl, or any of the meanings of $R^2$; and
(e) $R^1$ is (X—(Z)—)$_n$[($C_3$–$C_{10}$)cycloalkyl]—(Z')— wherein Z and Z' are individually ($C_1$–$C_6$)alkyl, optionally interrupted by 1–3 S or nonperoxide O, or is absent, and n is 1–3; or a pharmaceutically acceptable salt thereof; wherein said amount is effective to provide coronary artery vasodilation; and (b) performing a technique on said mammal selected from the soup consisting of myocardial perfusion imaging, ventricular function imaging and a method for measuring coronary blood flow velocity, to detect the presence and/or assess the severity of said coronary artery stenosis.

2. The method of claim 1 wherein the mammal is a human.

3. The method of claim 1 wherein 5'-X is —CH$_2$OH or —C(O)NR$^3$R$^4$.

4. The method of claim 1 wherein R$^3$ is H and R$^4$ is (C$_1$–C$_4$)alkyl.

5. The method of claim 1 wherein each R is H or (C$_1$–C$_4$)alkyl.

6. The method of claim 1 wherein Z' is —CH$_2$— or —CH$_2$—CH$_2$—.

7. The method of claim 6 wherein Z is —CH$_2$— or —CH$_2$—CH$_2$—.

8. The method of claim 1 wherein C$_3$–C$_{10}$ cycloalkyl comprises cyclohexyl or cyclopentyl.

9. The method of claim 8 wherein X is (C$_1$–C$_4$) alkoxycarbonyl, C(O)NR$^3$R$^4$ or acetoxymethyl.

10. The method of claim 7 wherein X is HO$_2$C—.

11. The method of claim 7 wherein X—Z and Z' are trans on cycloalkyl.

12. The method of claim 1 wherein R is H, 5'-X is ethylaminocarbonyl, and R$^1$—C≡C— is 2-(4-methoxycarbonyl-cyclohexylmethyl)ethynyl or 2-(4-carboxy-cyclohexylmethyl)ethynyl.

13. The method of claim 1 wherein R is H, 5'-X is ethylaminocarbonyl, and R$^1$—C≡C— is 2-(4-acetoxymethyl-cyclohexylmethyl)ethynyl.

14. The method of claim 1, wherein said coronary artery stenosis is due to coronary artery disease.

15. The method of claim 1 wherein said myocardial perfusion imaging is selected from the group consisting of planar scintigraphy, single photon emission computed tomography (SPECT), positron emission tomography (PET), nuclear magnetic resonance (NMR) imaging, perfusion contrast echocardiography, digital subtraction angiography (DSA) and ultrafast X-ray computed tomography (CINE CT).

16. The method of claim 15 wherein said myocardial perfusion imaging is selected from the group consisting of planar scintigraphy, single photon emission computed tomography (SPECT) and positron emission tomography (PET) used in conjunction with a radiopharmaceutical agent comprising a radionuclide selected from the group consisting of thallium-201, technetium-99m, nitrogen-13, rubidium-82, iodine-123 and oxygen-15.

17. The method of claim 16 wherein said myocardial perfusion imaging is scintigraphy and said radiopharmaceutical agent is thallium-201.

18. The method of claim 1 wherein said ventricular function imaging technique is selected from the group consisting of echocardiography, contrast ventriculography and radionuclide ventriculography.

19. The method of claim 1 wherein said ventricular function imaging technique is echocardiography.

20. The method of claim 1 wherein said method for measuring coronary blood flow velocity is selected from the group consisting of doppler flow catheter, digital subtraction angiography and radiopharmaceutical imaging techniques.

21. The method of claim 1 wherein said method for measuring coronary blood flow velocity is doppler flow catheter.

22. The method of claim 2 comprising the steps of:
  (a) administering to said human by intravenous infusion or by bolus injection an amount of a compound of formula I effective to provide coronary artery dilation;
  (b) administering a radiopharmaceutical agent comprising thallium-201 or technetium-99m to said human; and
  (c) performing the scintigraphy on said human in order to detect the presence and assess the severity of coronary artery disease.

23. The method of claim 22 wherein the radiopharmaceutical agent is Tc-99m-sestamibi.

24. The method of claim 3, wherein 5'-X is —C(O)NR$^3$R$^4$.

* * * * *

UNITED STATES PATENT AND TRADEMARK OFFICE
CERTIFICATE OF CORRECTION

PATENT NO. : 6,322,771 B1
DATED : November 27, 2001
INVENTOR(S) : Linden et al.

It is certified that error appears in the above-identified patent and that said Letters Patent is hereby corrected as shown below:

Column 1,
Line 67, delete "*Immnol.*" and insert -- *Immunol.* --, therefor.

Column 2,
Line 66, delete "anti-ischeric" and insert -- anti-ischemic --, therefor.

Column 3,
Line 15, delete "hydrainoadenosine" and insert -- hydrazinoadenosine --, therefor.
Line 64, delete "-OC(O)R$^2$CH$_2$OC(O)R$^2$" and insert -- -OC(O)R$^2$, CH$_2$OC(O)R$^2$ --, therefor.

Column 6,
Line 31, delete "R$_1$" and insert -- R$^1$ --, therefor

Column 12,
Line 39, delete "stiffed" and insert -- stirred --, therefor.

Column 13,
Line 13, delete "aminno" and insert -- amino --, therefor.
Line 66, delete "6amino" and insert --6-amino --, therefor.

Column 14,
Line 51, delete "a trial" and insert -- atrial --, therefor.

Column 16,
Line 53, after "halogen" insert -- , --, therefor.

UNITED STATES PATENT AND TRADEMARK OFFICE
CERTIFICATE OF CORRECTION

PATENT NO. : 6,322,771 B1
DATED : November 27, 2001
INVENTOR(S) : Linden et al.

It is certified that error appears in the above-identified patent and that said Letters Patent is hereby corrected as shown below:

<u>Column 17,</u>
Line 2, delete "soup" and insert -- group --, therefor.

Signed and Sealed this

Fourth Day of June, 2002

*Attest:*

*Attesting Officer*

JAMES E. ROGAN
*Director of the United States Patent and Trademark Office*